(12) United States Patent
Riddell et al.

(10) Patent No.: US 9,987,308 B2
(45) Date of Patent: Jun. 5, 2018

(54) METHOD AND COMPOSITIONS FOR CELLULAR IMMUNOTHERAPY

(75) Inventors: Stanley R. Riddell, Sammamish, WA (US); Michael Hudecek, Leipzig (DE)

(73) Assignee: Fred Hutchinson Cancer Research Center, Seattle, WA (US)

( * ) Notice: Subject to any disclaimer, the term of this patent is extended or adjusted under 35 U.S.C. 154(b) by 672 days.

(21) Appl. No.: 14/006,641

(22) PCT Filed: Mar. 23, 2012

(86) PCT No.: PCT/US2012/030388
§ 371 (c)(1),
(2), (4) Date: May 5, 2014

(87) PCT Pub. No.: WO2012/129514
PCT Pub. Date: Sep. 27, 2012

(65) Prior Publication Data
US 2014/0314795 A1    Oct. 23, 2014

Related U.S. Application Data

(60) Provisional application No. 61/466,552, filed on Mar. 23, 2011.

(51) Int. Cl.
| | | |
|---|---|---|
| *C12N 5/0783* | (2010.01) | |
| *A61K 35/17* | (2015.01) | |
| *C07K 14/725* | (2006.01) | |
| *C07K 16/28* | (2006.01) | |
| *C07K 16/30* | (2006.01) | |
| *A61K 39/00* | (2006.01) | |
| *A61K 35/12* | (2015.01) | |

(52) U.S. Cl.
CPC .......... *A61K 35/17* (2013.01); *C07K 14/7051* (2013.01); *C07K 16/28* (2013.01); *C07K 16/2803* (2013.01); *C07K 16/3061* (2013.01); *C12N 5/0636* (2013.01); *A61K 2035/122* (2013.01); *A61K 2035/124* (2013.01); *A61K 2039/5156* (2013.01); *A61K 2039/57* (2013.01); *A61K 2039/572* (2013.01); *C07K 2317/622* (2013.01); *C07K 2319/00* (2013.01); *C12N 2501/515* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 4,690,915 A | 9/1987 | Rosenberg | |
| 6,040,177 A | 3/2000 | Riddell et al. | |
| 2003/0170238 A1 | 9/2003 | Gruenberg et al. | |
| 2008/0131415 A1 | 6/2008 | Riddell et al. | |
| 2014/0314795 A1* | 10/2014 | Riddell | C07K 14/7051 424/184.1 |

FOREIGN PATENT DOCUMENTS

| | | |
|---|---|---|
| WO | WO 2006/060878 A1 | 6/2006 |
| WO | WO 2010/025177 A1 | 3/2010 |

OTHER PUBLICATIONS

Isolation of CD4+CD62L+ T cells, *Miltenyi Biotec* (4 pages) (2007).
Chang et al., "Transgene-enforced co-stimulation of CD4+ T cells leads to enhanced and sustained anti-tumor effector functioning," *Cytotherapy* 9(8):771-784 (2007).
Huang et al., "Sleeping Beauty Transposon-mediated Engineering of Human Primary T Cells for Therapy of CD19+ Lymphoid Malignancies," *Molecular Therapy* 16(3):580-589 (Mar. 2008).
Xie et al., "Naive tumor-specific CD4+ T cells differentiated in vivo eradicate established melanoma," *The Journal of Experimental Medicine* 207(3):651-667 (Feb. 15, 2010).
Altenschmidt et al., "Cytolysis of Tumor Cells Expressing the Neu/erbB-2, erbB-3, and erbB-4 Receptors by Genetically Targeted Naive T Lymphocytes," *Clinical Cancer Research* 2: 1001-1008, Jun. 1996.
Altenschmidt et al., "Adoptive Transfer of in Vitro-Targeted, Activated T Lymphocytes Results in Total Tumor Regression," *The Journal of Immunology* 159: 5509-5515, 1997.
Hinrichs et al., "Adoptively transferred effector cells derived from naïve rather than central memory CD8+ T cells mediate superior antitumor immunity," *PNAS* 106(41): 17469-17474, Oct. 13, 2009.
Hinrichs et al., "Human effector CD8+ T cells derived from naive rather than memory subsets possess superior traits for adoptive immunotherapy," *Blood* 117(3): 808-814, 2011.
Hudecek et al., "The B-cell tumor-associated antigen ROR1 can be targeted with T cells modified to express a ROR1-specific chimeric antigen receptor," *Blood* 116(22): 4532-4541, 2010.
Kershaw et al., "Gene-Engineered T Cells as a Superior Adjuvant Therapy for Metastatic Cancer," *The Journal of Immunology* 173: 2143-2150, 2004.
Moeller et al., "Adoptive transfer of gene-engineered CD4+ helper T cells induces potent primary and secondary tumor rejection," *Blood* 106: 2995-3003, 2005.
Teng et al.,"Immunotherapy of Cancer Using Systemically Delivered Gene-Modified Human T Lumphocytes," *Human Gene Therapy* 15: 699-708, Jul. 2004.
Walker et al., "Long-term in vivo survival of receptor-modified syngeneic T cells in patients with human immunodeficiency virus infection," *Blood* 96: 467-474, 2000.
Wang et al., "Engraftment of human central memory-derived effector CD8+ T cells in immunodeficient mice," *Blood* 117(6): 1888-1898, 2011.
Westwood et al., "Genetic redirection of T cells for cancer therapy," *Journal of Leukocyte Biology* 87: 791-803, May 2010.
Dotti et al., "Fifteen Years of Gene Therapy Based on Chimeric Antigen Receptors: Are We Nearly there Yet?" *Human Gene Therapy* 20:1229-1239 (Nov. 2009).

(Continued)

*Primary Examiner* — Michael Burkhart
(74) *Attorney, Agent, or Firm* — Seed IP Law Group LLP

(57) ABSTRACT

The present invention provides methods and compositions to confer and/or augment immune responses mediated by cellular immunotherapy, such as by adoptively transferring genetically modified tumor specific CD8+ T cells in the presence of tumor-specific, subset specific genetically modified CD4+ T cells, wherein the CD4+ T cells confer and/or augment a CD8+ T cells ability to sustain anti-tumor reactivity and increase and/or maximize tumor-specific proliferation of the tumor-specific CD8+ T cells of interest. Pharmaceutical formulations produced by the method, and methods of using the same, are also described.

31 Claims, 18 Drawing Sheets

(56) References Cited

OTHER PUBLICATIONS

Baskar et al., "Unique Cell Surface Expression of Receptor Tyrosine Kinase ROR1 in Human B-Cell Chronic Lymphocytic Leukemia," *Clin. Cancer Res.* 14(2): 396-404, Jan. 15, 2008.
Berger et al., "Adoptive transfer of effector CD8+ T cells derived from central memory cells establishes persistent T cell memory in primates," *The Journal of Clinical Investigation* 118(1): 294-305, Jan. 2008.
Berger et al., "Adoptive transfer of virus-specific and tumor-specific T cell immunity," *Current Opinion in Immunology* 21: 224-232, 2009.
Blattman et al., "Cancer Immunotherapy: A Treatment for the Masses," *Science* 305: 200-205, Jul. 9, 2004.
Bleakley et al., "Molecules and mechanisms of the graft-versus-leukaemia effect," *Nature Reviews Cancer* 4: 371-380, May 2004.
Bollard et al., "Cytotoxic T Lymphocyte Therapy for Epstein-Barr Virus+ Hodgkin's Disease," *J. Exp. Med.* 200(12): 1623-1633, Dec. 20, 2004.
Brentjens et al., "Eradication of systemic B-cell tumors by genetically targeted human T lymphocytes co-stimulated by CD80 and interleukin-15," *Nature Medicine* 9(3): 279-286, Mar. 2003.
Butcher et al., "Lymphocyte homing and homeostasis," *Science* 272(5258): 60, 1996, 13 pages.
Cheadle et al., "Natural Expression of the CD19 Antigen Impacts the Long-Term Engraftment but Not Antitumor Activity of CD19-Specific Engineered T Cells," *The Journal of Immunology* 184(4): 1885-1896, Jan. 20, 2010.
Cheever et al., "Specificity of adoptive chemoimmunotherapy of established syngeneic tumors," *The Journal of Immunology* 125(2): 711-714, Aug. 1980.
Dudley et al., "Adoptive Transfer of Cloned Melanoma-Reactive T Lymphocytes for the Treatment of Patients with Metastatic Melanoma," *Journal of Immunotherapy* 24(4): 363-373, 2001.
Dudley et al., "A phase I Study of Nonmyeloablative Chemotherapy and Adoptive Transfer of Autologous Tumor Antigen-Specific T Lymphocytes in Patients With Metastatic Melanoma," *J. Immunother.* 25(3): 243-251, 2002.
Dudley et al., "Cancer Regression and Autoimmunity in Patients After Clonal Repopulation with Antitumor Lymphocytes," *Science* 298(5594): 850-854, Oct. 25, 2002.
Dudley et al., "Adoptive Cell Transfer Therapy Following Non-Myeloablative but Lymphodepleting Chemotherapy for the Treatment of Patients With Refractory Metastatic Melanoma," *J. Clin. Oncol.* 23(10): 2346-2357, Apr. 1, 2005.
Fukuda et al., "Antisera induced by infusions of autologous Ad-CD154-leukemia B cells identify ROR1 as an oncofetal antigen and receptor for Wnt5a," *Proc. Natl. Acad. Sci. U S A* 105(8): 3047-3052, Feb. 26, 2008.
Gattinoni et al., "Acquisition of full effector function in vitro paradoxically impairs the in vivo antitumor efficacy of adoptively transferred CD8+ T cells," *The Journal of Clinical Investigation* 115(6): 1616-1626, Jun. 2005.
Gattinoni et al., "Adoptive immunotherapy for cancer: building on success," *Nat. Rev. Immunol.* 6(5): 383-393, May 2006.
Hudecek et al., "Naïve CD4+ T Cells Modified to Express a ROR1-Specific CAR Mediate Anti-Tumor Activity and Provide Superior Help to CD8+ ROR1-CAR T Cells," *Blood* (ASH Annual Meeting Abstracts) 118: Abstract 643, 2011, 3 pages.
Kessels et al., "Immunotherapy through TCR gene transfer," *Nature Immunology* 2(10): 957-961, Oct. 2001.

Klein et al., "Gene Expression Profiling of B Cell Chronic Lymphocytic Leukemia Reveals a Homogeneous Phenotype Related to Memory B Cells," *J. Exp. Med.* 194(11): 1625-1638, Dec. 3, 2001.
Lapalombella et al., "Lenalidomide treatment promotes CD154 expression on CLL cells and enhances production of antibodies by normal B cells through a PI3-kinase-dependent pathway," *Blood* 115(13): 2619-2629, Apr. 1, 2010.
Mitsuyasu et al., "Prolonged survival and tissue trafficking following adoptive transfer of CD4ζ gene-modified autologous CD4+ and CD8+ T cells in human immunodeficiency virus-infected subjects," *Blood* 96(3): 785-793, Aug. 2000.
Morgan et al., "Cancer Regression in Patients After Transfer of Genetically Engineered Lymphocytes," *Science* 314(5796): 126-129, Oct. 6, 2006.
Pahl-Seibert et al., "Highly Protective In Vivo Function of Cytomegalovirus IE1 Epitope-Specific Memory CD8 T Cells Purified by T-Cell Receptor-Based Cell Sorting," *Journal of Virology* 79(9): 5400-5413, May 2005.
Riddell et al., "The use of anti-CD3 and anti-CD28 monoclonal antibodies to clone and expand human antigen-specific T cells," *Journal of Immunological Methods* 128: 189-201, 1990.
Riddell et al., "Restoration of Viral Immunity in Immunodeficient Humans by the Adoptive Transfer of T Cell Clones," *Science* 257: 238-241, Jul. 10, 1992.
Rooney et al., "Infusion of Cytotoxic T Cells for the Prevention and Treatment of Epstein-Barr Virus-Induced Lymphoma in Allogeneic Transplant Recipients," *Blood* 92(5): 1549-1555, Sep. 1, 1998.
Rosenwald et al., "Relation of Gene Expression Phenotype to Immunoglobulin Mutation Genotype in B Cell Chronic Lymphocytic Leukemia," *The Journal of Experimental Medicine* 194(11): 1639-1647, Dec. 3, 2001.
Sallusto et al., "Central Memory and Effector Memory T Cell Subsets: Function, Generation, and Maintenance," *Annu. Rev. Immunol.* 22: 745-763, 2004.
Schmitt et al., "Maintenance of T Cell Specification and Differentiation Requires Recurrent Notch Receptor-Ligand Interactions," *J. Exp. Med.* 200(4): 469-479, Aug. 16, 2004.
Singh et al., "Selective Reprogramming of CD 19-Specific T Cells with IL-21 and CD28 Signaling for Adoptive Immunotherapy of Acute Lymphoblastic Leukemia," *Biology of Blood and Marrow Transplantation* 15(2): 61-62, Feb. 1, 2009, Abstract No. 164, 2 pages.
Stanislawski et al., "Circumventing tolerance to a human MDM2-derived tumor antigen by TCR gene transfer," *Nature Immunology* 2(10): 962-970, Oct. 2001.
Walter et al., "Reconstitution of cellular immunity against cytomegalovirus in recipients of allogeneic bone marrow by transfer of T-cell clones from the donor," *N. Engl. J. Med.* 333: 1038-1044, Oct. 19, 1995.
Wang et al., Cellular Immunotherapy for Follicular Lymphoma Using Genetically Modified CD20-Specific CD8+ Cytotoxic T Lymphocytes, *Molecular Therapy* 9(4): 577-586, Apr. 2004.
Yee et al., "Adoptive T cell therapy using antigen-specific CD8+ T cell clones for the treatment of patients with metastatic melanoma: In vivo persistence, migration, and antitumor effect of transferred T cells," *Proc. Natl. Acad. Sci. USA* 99(25): 16168-16173, Dec. 10, 2002.
Lamers et al., "Immune responses to transgene and retroviral vector in patients treated with ex vivo-engineered T cells," *Blood* 117(1):72-82 (Jan. 6, 2011).

\* cited by examiner

IFNg ELISA

Multiplex cytokine assay (Luminex)

CD4+ N CD19 - CAR          CD4+ N control
d19 after T - cell infusion

Mouse treated with CD8+ CAR T cells alone

Mouse treated with combined CD8+ and CD4+ CAR T cells

METHOD AND COMPOSITIONS FOR CELLULAR IMMUNOTHERAPY

This application is being filed on 23 Mar. 2012, as a PCT International Patent application in the name of Fred Hutchinson Cancer Research Center, a U.S. national corporation, applicant for the designation of all countries except the U.S., and, Stanley R. Riddell, a citizen of Canada, and Michael Hudecek, a citizen of Germany, applicants for the designation of the U.S. only, and claims priority to U.S. Patent Application Ser. No. 61/466,552 filed on 23 Mar. 2011, the disclosure of which is incorporated herein by reference in its entirety.

STATEMENT REGARDING FEDERALLY SPONSORED RESEARCH

This invention was made with government support under CA018029 awarded by the National Institutes of Health. The government has certain rights in the invention.

FIELD OF THE INVENTION

The present invention relates to the field of biomedicine and specifically methods useful for cancer therapy. In particular, embodiments of the invention relate to methods and compositions for carrying out cellular immunotherapy.

BACKGROUND OF THE INVENTION

Studies in rodents have demonstrated that adoptive immunotherapy with antigen specific T cells is effective for cancer and infections, and there is evidence this modality has therapeutic activity in humans[1-8]. For clinical applications, it is necessary to isolate T cells of a desired antigen specificity or to engineer T cells to express receptors that target infected or transformed cells, and then expand these cells in culture[9-14]. The transfer of T cell clones is appealing because it enables control of specificity and function, and facilitates evaluation of in vivo persistence, toxicity and efficacy. Additionally, in the setting of allogeneic stem cell transplantation, the administration to recipients of T cell clones from the donor that target pathogens or malignant cells can avoid graft-versus-host disease that occurs with infusion of unselected donor T cells[3,4,15]. However, it is apparent from clinical studies that the efficacy of cultured T cells, particularly cloned CD8+ T cells, is frequently limited by their failure to persist after adoptive transfer[16,17].

The pool of lymphocytes from which T cells for adoptive immunotherapy can be derived contains naïve and long-lived, antigen experienced memory T cells ($T_M$). $T_M$ can be divided further into subsets of central memory ($T_{CM}$) and effector memory ($T_{EM}$) cells that differ in phenotype, homing properties and function[18]. CD8+ $T_{CM}$ express CD62L and CCR7 at the cell surface, which promote migration into lymph nodes, and proliferate rapidly if re-exposed to antigen. CD8+ $T_{EM}$ lack cell surface CD62L and preferentially migrate to peripheral tissues, and exhibit immediate effector function[19]. In response to antigen stimulation, CD8+ $T_{CM}$ and $T_{EM}$ both differentiate into cytolytic effector T cells ($T_E$) that express a high level of granzymes and perforin, but are short-lived[20]. Thus, the poor survival of T cells in clinical immunotherapy trials may simply result from their differentiation during in vitro culture to $T_E$ that are destined to die[17,21,22]. There is a need to identify cell populations and methods that provide enhanced survival of adoptively transferred T cells in vivo.

SUMMARY OF THE INVENTION

In one aspect, the present invention relates to methods and compositions to confer and/or augment immune responses mediated by cellular immunotherapy, such as by adoptively transferring tumor-specific, subset specific genetically modified CD4+ T cells, wherein the CD4+ T cells confer and/or augment the ability of CD8+ T cells to sustain anti-tumor reactivity and increase and/or maximize tumor-specific proliferation.

In one embodiment, the present invention provides a method of performing cellular immunotherapy in a subject having a disease or disorder by administering to the subject a genetically modified cytotoxic T lymphocyte cell preparation that provides a cellular immune response, wherein the cytotoxic T lymphocyte cell preparation comprises CD8+ T cells that have a chimeric antigen receptor with an extracellular antibody variable domain specific for an antigen associated with the disease or disorder and an intracellular signaling domain of a T cell or other receptors, such as co-stimulatory domains; and a genetically modified helper T lymphocyte cell preparation that exhibits a predominant Th1 phenotype as well as produce other cytokines, elicits direct tumor recognition and augments the genetically modified cytotoxic T lymphocyte cell preparations ability to mediate a cellular immune response, wherein the helper T lymphocyte cell preparation comprises CD4+ T cells that have a chimeric antigen receptor comprising an extracellular antibody variable domain specific for the antigen associated with the disease or disorder and an intracellular signaling domain of a T cell receptor. Various modifications of the above method are possible. For example, the chimeric antigen receptor modifying the CD4+ T cell and the CD8+ T cell can be the same or different. In alternative embodiments, the T cells can be modified with a recombinant T cell receptor (TCR). TCR could be specific for any antigen, pathogen or tumor. There are TCRs for many tumor antigens in melanoma (MART1, gp100, for example), leukemia (WT1, minor histocompatibility antigens, for example), breast cancer (her2, NY-BR1, for example).

In another embodiment, the present invention provides an adoptive cellular immunotherapy composition having a genetically modified CD8+ cytotoxic T lymphocyte cell preparation that elicits a cellular immune response, wherein the cytotoxic T lymphocyte cell preparation comprises CD8+ T cells that have a chimeric antigen receptor with an extracellular variable domain antibody specific for an antigen associated with the disease or disorder and an intracellular signaling domain of a T cell or other receptors, such as a costimulatory domain, and a genetically modified helper T lymphocyte cell preparation that exhibits a predominant Th1 phenotype as well as produce other cytokines, elicits direct tumor recognition and augments the ability of genetically modified cytotoxic T lymphocyte cell preparations to mediate a cellular immune response, wherein the helper T lymphocyte cell preparation has CD4+ T cells that have a chimeric antigen receptor with an extracellular antibody variable domain specific for the antigen associated with the disease or disorder and an intracellular signaling domain of a T cell receptor.

In yet another embodiment, the present invention provides an adoptive cellular immunotherapy composition having a chimeric antigen receptor modified tumor-specific CD8+ cytotoxic T lymphocyte cell preparation that elicits a cellular immune response, wherein the cytotoxic T lymphocyte cell preparation comprises CD8+ T cells that have a chimeric antigen receptor comprising an extracellular single chain antibody specific for an antigen associated with the disease or disorder and an intracellular signaling domain of a T cell receptor, and an antigen-reactive chimeric antigen receptor modified naïve CD4+ T helper cell that is derived from CD45RO negative, CD62L positive CD4 positive T cells, and a pharmaceutically acceptable carrier.

In another embodiment, the present invention provides an adoptive cellular immunotherapy composition having an antigen specific CD8+ cytotoxic T lymphocyte cell preparation that elicits a cellular immune response comprising CD8+ T cells derived from the patient together with an antigen-reactive chimeric antigen receptor modified CD4+ T helper cell that elicits a Th1 cytokine response and augments the CD8+ immune response to pathogens, wherein the helper T lymphocyte cell preparation with CD4+ T cells that have a chimeric antigen receptor with an extracellular antibody variable domain specific for the antigen associated with the disease or disorder and an intracellular signaling domain of a T cell receptor.

In another embodiment, the present invention provides an adoptive cellular immunotherapy composition with an antigen-reactive chimeric antigen receptor modified CD4+ T helper cell that elicits direct tumor recognition and augments the CD8+ immune response to pathogens, wherein the helper T lymphocyte cell preparation comprises CD4+ T cells that have a chimeric antigen receptor comprising an extracellular antibody variable domain specific for an antigen associated with a disease or disorder and an intracellular signaling domain of a T cell receptor.

In another aspect, the present invention provides a method of manufacturing an adoptive immunotherapy composition by obtaining a chimeric antigen receptor modified tumor-specific CD8+ cytotoxic T lymphocyte cell preparation that elicits a cellular immune response and an antigen-reactive chimeric antigen receptor, wherein the modified cytotoxic T lymphocyte cell preparation comprises CD8+ T cells that have a chimeric antigen receptor with an extracellular antibody variable domain specific for an antigen associated with the disease or disorder and an intracellular signaling module of a T cell receptor; and obtaining a modified naïve CD4+ T helper cell that elicits a Th1 cytokine response, wherein the modified helper T lymphocyte cell preparation comprises CD4+ cells that have a chimeric antigen receptor with an extracellular antibody variable domain specific for the antigen associated with the disease or disorder and an intracellular signaling domain of a T cell receptor.

In another embodiment, the present invention provides a method of manufacturing an adoptive immunotherapy composition by obtaining a modified naïve CD4+ T helper cell that elicits a Th1 cytokine response, wherein the modified helper T lymphocyte cell preparation comprises CD4+ T cells that have a chimeric antigen receptor comprising an extracellular antibody variable domain specific for the antigen associated with the disease or disorder and an intracellular signaling domain of a T cell receptor, and combining the modified naïve CD4+ T helper cell with an antigen specific central memory CD8+ cytotoxic T lymphocyte cell preparation that has a chimeric antigen receptor with an extracellular antibody variable domain specific for the antigen associated with the disease or disorder and an intracellular signaling domain of a T cell or other receptors.

In one embodiment, the present invention provides a method of performing cellular immunotherapy in subject having a disease or disorder by administering to the subject a genetically modified helper T lymphocyte cell preparation, wherein the modified helper T lymphocyte cell preparation comprises CD4+ T cells that have a chimeric antigen receptor comprising an extracellular antibody variable domain specific for an antigen associated with the disease or disorder and an intracellular signaling module of a T cell receptor.

These and other embodiments of the invention are described further in the accompanying specification, drawings and claims.

BRIEF DESCRIPTION OF THE DRAWINGS

FIG. 8: (i.e., FIGS. 8A-8D, collectively) shows the generation of CD4+ CAR T cell lines from flow sort purified CD4+ naïve, central memory and effector memory subsets and analysis of T-cell function. Cytokine profile and proliferative capacity suggest that CD4+ ROR1-CAR T cells derived from naïve CD4+ T cells may be best suited to provide help to CD8+ CTLs. Similar data were obtained in experiments comparing the function of CD4+ CAR T-cell lines expressing a CD19-specific CAR.

DETAILED DESCRIPTION OF THE PREFERRED EMBODIMENTS

Figure 1:
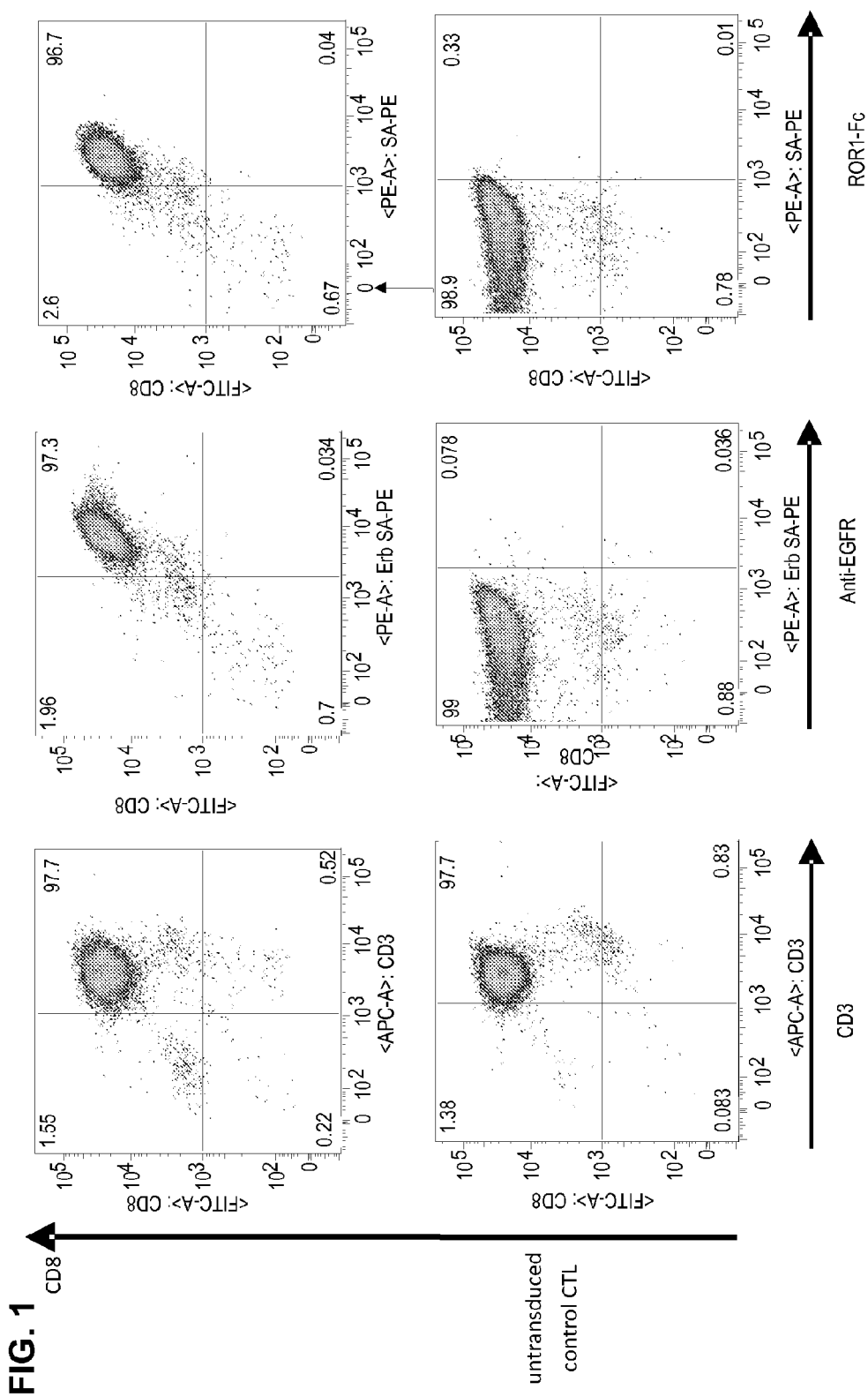
FIG. 1: shows the phenotype and analysis of chimeric antigen receptor (CAR) expression in a CAR-transduced with ROR1-CAR encoding lentivirus, and an untransduced CD8+ T cell line as a control. The ROR1-CAR cassette contains a truncated EGFR that serves as transduction marker and can be detected by staining with anti-EGFR monoclonal antibodies. Truncated Fc-ROR1 fusion protein binds directly to the antigen-binding domain of the ROR1-CAR and selectively stains the ROR1-CAR transduced but not the untransduced control T cell line. Expression of the ROR1-CAR on the cell surface of CD8+ T cells is measured directly by binding to ROR1-Fc fusion protein and indirectly by expression of a truncated EGFR that is encoded downstream of a 2A sequence in the vector.

"T cells" or "T lymphocytes" as used herein may be from any mammalian, preferably primate, species, including monkeys, dogs, and humans. In some embodiments the T cells are allogeneic (from the same species but different donor) as the recipient subject; in some embodiments the T cells are autologous (the donor and the recipient are the same); in some embodiments the T cells are syngeneic (the donor and the recipients are different but are identical twins).

Cytotoxic T lymphocyte (CTL) as used herein refers to a T lymphocyte that expresses CD8 on the surface thereof (i.e., a CD8+ T cell). In some embodiments such cells are preferably "memory" T cells ($T_M$ cells) that are antigen-experienced.

"Central memory" T cell (or "$T_{CM}$") as used herein refers to an antigen experienced CTL that expresses CD62L and CD45RO on the surface thereof, and does not express or has decreased expression of CD45RA as compared to naïve cells. In embodiments, central memory cells are positive for expression CD62L, CCR7, CD28, CD127, CD45RO, and CD95, and have decreased expression of CD54RA as compared to naïve cells.

"Effector memory" T cell (or "$T_{EM}$") as used herein refers to an antigen experienced CTL that does not express or has decreased expression of CD62L on the surface thereof as compared to central memory cells, and does not express or has decreased expression of CD45RA as compared to naïve cell. In embodiments, effector memory cells are negative for expression CD62L, CCR7, CD28, CD45RA, and are positive for CD127 as compared to naïve cells or central memory cells.

"Naïve" T cells as used herein refers to a non antigen experienced T lymphocyte that expresses CD62L and CD45RA, and does not express or has decreased expression of CD45RO– as compared to central memory cells. In some embodiments, naïve CD8+ T lymphocytes are characterized by the expression of phenotypic markers of naïve T cells including CD62L, CCR7, CD28, CD3, CD127, and CD45RA.

"Effector" "$T_E$" T cells as used herein refers to a antigen experienced cytotoxic T lymphocyte cells that do not express or have decreased expression of CD62L, CCR7, CD28, and are positive for granzyme B and perforin as compared to central memory cells.

"Enriched" and "depleted" as used herein to describe amounts of cell types in a mixture refers to the subjecting of the mixture of the cells to a process or step which results in an increase in the number of the "enriched" type and a decrease in the number of the "depleted" cells. Thus, depending upon the source of the original population of cells subjected to the enriching process, a mixture or composition may contain 60, 70, 80, 90, 95, or 99 percent or more (in number or count) of the "enriched" cells and 40, 30, 20, 10, 5 or 1 percent or less (in number or count) of the "depleted" cells.

Interleukin-15 is a known and described in, for example, U.S. Pat. No. 6,344,192.

"CAR" as used herein refers to chimeric antigen receptor comprising an extracellular variable domain of an antibody specific for an antigen associated with the disease or disorder and an intracellular signaling domain of a T cell or other receptors, such as a costimulatory domain.

MODES OF THE DISCLOSURE

CD4+ T lymphocytes during in vitro culture significantly increase proliferation, persistence and anti-tumor reactivity of tumor-specific CD8+ T cells in vitro and in vivo. In some embodiments, naïve CD4+ T cells possess an intrinsic programming that leads to superior helper activity compared to CD4+ T cells derived from central and effector memory, or bulk CD4+ T cells.

In embodiments, tumor-reactive CD4+ T cells are modified with a single-chain antibody-derived chimeric antigen receptor (CAR) specific for the orphan tyrosine kinase receptor ROR1 or for the CD19 molecule. ROR1 is uniformly expressed on chronic lymphocytic leukemia (CLL) and mantle cell lymphoma (MCL) and ROR1-specific CAR from an anti-ROR1 monoclonal antibody (mAb) confers specific recognition of malignant, but not mature normal B-cells when expressed in CD8+ cytotoxic T cells (CTLs). ROR1-CAR T cells from bulk and flow sort purified naïve, central and effector memory CD4+ T cells are obtained from the peripheral blood of both healthy donors and CLL patients. CD4+ CAR T cells had specific but weak cytolytic activity against ROR1+ tumors including primary CLL, the MCL line Jeko-1, and K562 cells transfected with ROR1. Multiplex cytokine analysis detects high-level production of Th1 cytokines with significantly higher levels of IFNγ, TNFa, and particularly IL-2 compared to CD8+ CAR CTLs. CFSE staining shows dramatically higher proliferation after stimulation with ROR1-positive tumor cells, with both the percentage of cells that were induced to proliferate and the number of cell divisions that the proliferating subset underwent being significantly higher compared to CD8+ CAR CTL. CD4+ T cells obtained from both healthy donors and CLL patients acquire anti-tumor reactivity after genetic modification with a ROR1-specific CAR. Moreover, the ability to proliferate in the absence of exogenous cytokines and to produce high levels of Th1 cytokines demonstrates that CD4+ CAR T cells exert typical helper functions after stimulation through the CAR and suggests that in addition to conferring direct anti-tumor effects, could be utilized to augment tumor-specific CD8+ CTL.

The cytokine profile and proliferative capacity of ROR1-CAR T cells derived from flow sort purified CD4+ naïve, central and effector memory subsets is obtained. The CD4+ CAR T cells, derived from the naïve CD45RA+CD45RO-CD62L+ subset, produces the highest levels of Th1 cytokines, especially IL-2, and proliferates in response to ROR1+ tumor cells. Indeed, in co-culture experiments, the addition of CAR-transduced, but not untransduced CD4+ T cells leads to a significant increase in tumor-specific proliferation of CD8+ CAR CTLs. In some embodiments, CAR-modified CD4+ T cells derived from naïve rather than central and effector memory subsets or bulk CD4+ T cells results in enhanced proliferation of CD8+ CAR CTL.

CD8+ central memory T cells have an intrinsic programming that allows them to persist for extended periods after administration, which makes them the preferred subset of CD8+ T cells for immunotherapy. In embodiments, ROR1-CAR or CD19 CAR modified CTLs from sort purified CD8+ central memory T cells and CD4+ naïve CAR-modified T cells provide enhanced proliferation of the CD8+ T cell subset. In embodiments, tumor-specific CD4+ T cells exert anti-tumor reactivity and provide help to tumor-specific CD8+ T cells in vitro and in vivo. In a specific embodiment, tumor-specific CD4+ T cells from the naïve subset are utilized.

In another embodiment, the CD8+ and CD4+ T cells can be modified with a T cell receptor (TCR). The TCR could be specific for any antigen, pathogen or tumor (there are TCRs for many tumor antigens in melanoma (MART1, gp100 for example), leukemia (WT1, minor histocompatibility antigens for example), breast cancer (her2, NY-BR1 for example).

DETAILED DESCRIPTION

Compositions

The disclosure provides for an adoptive cellular immunotherapy composition comprising a genetically modified helper T lymphocyte cell preparation that augments the genetically modified cytotoxic T lymphocyte cell preparations ability to mediate a cellular immune response, wherein the helper T lymphocyte cell preparation comprises CD4+ T cells that have a chimeric antigen receptor comprising an extracellular antibody variable domain specific for the antigen associated with the disease or disorder and an intracellular signaling domain of a T cell receptor or other receptors.

In some embodiments, an adoptive cellular immunotherapy composition further comprises a chimeric antigen receptor modified tumor-specific CD8+ cytotoxic T lymphocyte cell preparation that elicits a cellular immune response, wherein the cytotoxic T lymphocyte cell preparation comprises CD8+ T cells that have a chimeric antigen receptor comprising an extracellular single chain antibody specific for an antigen associated with the disease or disorder and an intracellular signaling domain of a T cell receptor.

In some embodiments, an adoptive cellular immunotherapy composition comprises a chimeric antigen receptor modified tumor-specific CD8+ cytotoxic T lymphocyte cell preparation that elicits a cellular immune response, wherein the cytotoxic T lymphocyte cell preparation comprises CD8+ T cells that have a chimeric antigen receptor comprising an extracellular single chain antibody specific for an antigen associated with the disease or disorder and an intracellular signaling domain of a T cell receptor, in combination with an antigen-reactive chimeric antigen receptor modified naïve CD4+ T helper cell derived from CD45RO negative, CD62L positive CD4 positive T cells, and a pharmaceutically acceptable carrier.

In other embodiments, an adoptive cellular immunotherapy composition comprises an antigen specific CD8+ cytotoxic T lymphocyte cell preparation that elicits a cellular immune response derived from the patient combined with an antigen-reactive chimeric antigen receptor modified naïve CD4+ T helper cell that augments the CD8+ immune response, wherein the helper T lymphocyte cell preparation comprises CD4+ T cells that have a chimeric antigen receptor comprising an extracellular antibody variable domain specific for the antigen associated with the disease or disorder and an intracellular signaling domain of a T cell receptor.

In a further embodiment, an adoptive cellular immunotherapy composition comprises an antigen-reactive chimeric antigen receptor modified naïve CD4+ T helper cell that augments the CD8+ immune response, wherein the helper T lymphocyte cell preparation comprises CD4+ T cells that have a chimeric antigen receptor comprising an extracellular antibody variable domain specific for an antigen associated with a disease or disorder and an intracellular signaling domain of a T cell receptor.

In embodiments, the CD4+ T helper lymphocyte cell is selected from the group consisting of naïve CD4+ T cells, central memory CD4+ T cells, effector memory CD4+ T cells, or bulk CD4+ T cells. In some embodiments, CD4+ helper lymphocyte cell is a naïve CD4+ T cell, wherein the naïve CD4+ T cell comprises a CD45RO−, CD45RA+, CD62L+CD4+ T cell. In embodiments, the CD8+ T cytotoxic lymphocyte cell is selected from the group consisting of naïve CD8+ T cells, central memory CD8+ T cells, effector memory CD8+ T cells or bulk CD8+ T cells. In some embodiments, the CD8+ cytotoxic T lymphocyte cell is a central memory T cell wherein the central memory T cell comprises a CD45RO+, CD62L+, CD8+ T cell. In yet other embodiments, the CD8+ cytotoxic T lymphocyte cell is a central memory T cell and the CD4+ helper T lymphocyte cell is a naïve CD4+ T cell.

In alternative embodiments, the T cells can be modified with a recombinant T cell receptor. TCR could be specific for any antigen, pathogen or tumor. There are TCRs for many tumor antigens in melanoma (MART1, gp100, for example), leukemia (WT1, minor histocompatibility antigens, for example), breast cancer (her2, NY-BR1, for example).

Selection and Sorting of T Lymphocyte Populations

The compositions described herein provide for antigen reactive CD4+ and CD8+ T lymphocytes.

T lymphocytes can be collected in accordance with known techniques and enriched or depleted by known techniques such as affinity binding to antibodies such as flow cytometry and/or immunomagnetic selection. After enrichment and/or depletion steps, in vitro expansion of the desired T lymphocytes can be carried out in accordance with known techniques (including but not limited to those described in U.S. Pat. No. 6,040,177 to Riddell et al.), or variations thereof that will be apparent to those skilled in the art.

For example, the desired T cell population or subpopulation may be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). The non-dividing feeder cells can comprise gamma-irradiated PBMC feeder cells. In some embodiments, the PBMC are irradiated with gamma rays in the range of about 3000 to 3600 rads. The order of addition of the T cells and feeder cells to the culture media can be reversed if desired. The culture can typically be incubated under conditions of temperature and the like that are suitable for the growth of T lymphocytes. For the growth of human T lymphocytes, for example, the temperature will generally be at least about 25 degrees Celsius, preferably at least about 30 degrees, more preferably about 37 degrees.

The T lymphocytes expanded include cytotoxic T lymphocytes (CTL) and helper T lymphocytes that are specific for an antigen present on a human tumor or a pathogen.

Optionally, the expansion method may further comprise the step of adding non-dividing EBV-transformed lymphoblastoid cells (LCL) as feeder cells. LCL can be irradiated with gamma rays in the range of about 6000 to 10,000 rads. The LCL feeder cells may be provided in any suitable amount, such as a ratio of LCL feeder cells to initial T lymphocytes of at least about 10:1.

Optionally, the expansion method may further comprise the step of adding anti-CD3 monoclonal antibody to the culture medium (e.g., at a concentration of at least about 0.5 ng/ml). Optionally, the expansion method may further comprise the step of adding IL-2 and/or IL-15 to the culture medium (e.g., wherein the concentration of IL-2 is at least about 10 units/ml).

After isolation of T lymphocytes both cytotoxic and helper T lymphocytes can be sorted into naïve, memory, and effector T cell subpopulations either before or after exoansion.

CD8+ cells can be obtained by using standard methods. In some embodiments, CD8+ cells are further sorted into naïve, central memory, and effector cells by identifying cell surface antigens that are associated with each of those types of CD8+ cells. In embodiments, memory T cells are present in both CD62L+ and CD62L− subsets of CD8+ peripheral blood lymphocytes. PBMC are sorted into CD62L−CD8+ and CD62L+CD8+ fractions after staining with anti-CD8 and anti-CD62L antibodies. In some embodiments, the expression of phenotypic markers of central memory TCM include CD45RO, CD62L, CCR7, CD28, CD3, and CD127 and are negative for granzyme B. In some embodiments, central memory T cells are CD45RO+, CD62L+, CD8+ T cells. In some embodiments, effector $T_E$ are negative for CD62L, CCR7, CD28, and CD127, and positive for granzyme B and perforin. In some embodiments, naïve CD8+ T lymphocytes are characterized by the expression of phenotypic markers of naïve T cells including CD62L, CCR7, CD28, CD3, CD127, and CD45RA.

Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, positive refers to uniform staining of the cell population above the isotype control. In some embodiments, a decrease in expression of one or markers refers to loss of 1 log 10 in the mean fluorescence intensity and/or decrease of percentage of cells that exhibit the marker of at least 20% of the cells, 25% of the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 20 and 100% when compared to a reference cell population. In some embodiments, a cell population positive for of one or markers refers to a percentage of cells that exhibit the marker of at least 50% of the cells, 55% of the cells, 60% of the cells, 65% of the cells, 70% of the cells, 75% of the cells, 80% of the cells, 85% of the cells, 90% of the cell, 95% of the cells, and 100% of the cells and any % between 50 and 100% when compared to a reference cell population.

CD4+ T helper cells are sorted into naïve, central memory, and effector cells by identifying cell populations that have cell surface antigens. CD4+ lymphocytes can be obtained by standard methods. In some embodiments, naïve CD4+ T lymphocytes are CD45RO−, CD45RA+, CD62L+ CD4+ T cell. In some embodiments, central memory CD4+ cells are CD62L positive and CD45RO positive. In some embodiments, effector CD4+ cells are CD62L and CD45RO negative.

Populations of CD4+ and CD8+ that are antigen specific can be obtained by stimulating naïve or antigen specific T lymphocytes with antigen. For example, antigen specific T cell clones can be generated to Cytomegalovirus antigens by isolating T cells from infected subjects and stimulating the cells in vitro with the same antigen. Naïve T cells may also be used. Any number of antigens from tumor cells, cancer cells, or infectious agents may be utilized. Examples of such antigens include HIV antigens, HCV antigens, HBV antigens, CMV antigens, parasitic antigens, and tumor antigens such as orphan tyrosine kinase receptor ROR1, tEGFR, Her2, L1-CAM, CD19, CD20, CD22, mesothelin, and CEA. In some embodiments, the adoptive cellular immunotherapy compositions are useful in the treatment of a disease or disorder including a solid tumor, hematologic malignancy, melanoma, or infection with a virus.

Modification of T Lymphocyte Populations

In some embodiments it may be desired to introduce functional genes into the T cells to be used in immunotherapy in accordance with the present disclosure. For example, the introduced gene or genes may improve the efficacy of therapy by promoting the viability and/or function of transferred T cells; or they may provide a genetic marker to permit selection and/or evaluation of in vivo survival or migration; or they may incorporate functions that improve the safety of immunotherapy, for example, by making the cell susceptible to negative selection in vivo as described by Lupton S. D. et al., *Mol. and Cell Biol.*, 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. This can be carried out in accordance with known techniques (see, e.g., U.S. Pat. No. 6,040,177 to Riddell et al. at columns 14-17) or variations thereof that will be apparent to those skilled in the art based upon the present disclosure.

In embodiments, T cells are modified with chimeric antigen receptors (CAR). In some embodiments, CARs comprise a single-chain antibody fragment (scFv) that is derived from the variable heavy (VH) and variable light (VL) chains of a monoclonal antibody (mAb) linked to the TCR CD3+ chain that mediates T-cell activation and cytotoxicity. Costimulatory signals can also be provided through the CAR by fusing the costimulatory domain of CD28 or 4-1BB to the CD3+ chain. CARs are specific for cell surface molecules independent from HLA, thus overcoming the limitations of TCR-recognition including HLA-restriction and low levels of HLA-expression on tumor cells.

CARs can be constructed with a specificity for any cell surface marker by utilizing antigen binding fragments or antibody variable domains of, for example, antibody molecules. The antigen binding molecules can be linked to one or more cell signaling modules. In embodiments, cell signaling modules include CD3 transmembrane domain, CD3 intracellular signaling domains, and CD 28 transmembrane domains. In embodiments, the intracellular signaling domain comprises a CD28 transmembrane and signaling domain linked to a CD3 intracellular domain. In some embodiments, a CAR can also include a transduction marker such as tEGFR.

In embodiments, the intracellular signaling domain of the CD8+ cytotoxic T cells is the same as the intracellular signaling domain of the CD4+ helper T cells. In other embodiments, the intracellular signaling domain of the CD8+ cytotoxic T cells is different than the intracellular signaling domain of the CD4+ helper T cells.

In some embodiments, the CD8+ T cell and the CD4+ T cell are both genetically modified with an antibody heavy chain domain that specifically binds a pathogen-specific cell surface antigen. In embodiments, CARs are specific for cell surface expressed antigens associated with pathogens, tumors, or cancer cells. In some embodiments, a CAR is specific for HIV antigens, HCV antigens, HBV antigens, CMV antigens, parasitic antigens, and tumor antigens such as orphan tyrosine kinase receptor ROR1, tEGFR, Her2, L1-CAM, CD19, CD20, CD22, mesothelin, and CEA. Methods for producing a CAR are described herein and can also be found in U.S. Pat. No. 6,410,319 by Forman and WO 2002/077029, U.S. Pat. No. 7,446,191, 2010/065818, 2010/ 025177, 2007/059298, and U.S. Pat. No. 7,514,537 by Jensen et al. and as described by Berger C. et al., *J. Clinical Investigation*, 118:1 294-308 (2008), which are hereby incorporated by reference.

In embodiments, the same or a different CAR can be introduced into each of CD4+ and CD8+ T lymphocytes. In embodiments, the CAR in each of these populations has an antigen binding molecule that specifically binds to the same antigen. The cellular signaling modules can differ. In embodiments each of the CD4 or CD8 T lymphocytes can be sorted in to naïve, central memory, effector memory or effector cells prior to transduction. In alternative embodiments, each of the CD4 or CD8 T lymphocytes can be sorted in to naïve, central memory, effector memory, or effector cells prior to transduction.

In alternative embodiments, the T cells can be modified with a recombinant T cell receptor. TCR could be specific for any antigen, pathogen or tumor. There are TCRs for many tumor antigens in melanoma (MART1, gp100 for example), leukemia (WT1, minor histocompatibility antigens for example), breast cancer (her2, NY-BR1 for example).

Various infection techniques have been developed which utilize recombinant infectious virus particles for gene delivery. This represents a currently preferred approach to the transduction of T lymphocytes of the present invention. The viral vectors which have been used in this way include virus vectors derived from simian virus 40, adenoviruses, adeno-associated virus (AAV), lentiviral vectors, and retroviruses. Thus, gene transfer and expression methods are numerous but essentially function to introduce and express genetic material in mammalian cells. Several of the above techniques have been used to transduce hematopoietic or lymphoid cells, including calcium phosphate transfection, protoplast fusion, electroporation, and infection with recombinant adenovirus, adeno-associated virus and retrovirus vectors. Primary T lymphocytes have been successfully transduced by electroporation and by retroviral infection.

Retroviral vectors provide a highly efficient method for gene transfer into eukaryotic cells. Moreover, retroviral integration takes place in a controlled fashion and results in the stable integration of one or a few copies of the new genetic information per cell.

It is contemplated that overexpression of a stimulatory factor (for example, a lymphokine or a cytokine) may be toxic to the treated individual. Therefore, it is within the scope of the invention to include gene segments that cause the T cells of the invention to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-I TK) gene (Wigler et al., Cell 11:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some embodiments it may be useful to include in the T cells a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine daminase gene (ADA), and the multi-drug resistance (MDR) gene.

Preferably, the positive selectable marker and the negative selectable element are linked such that loss of the negative selectable element necessarily also is accompanied by loss of the positive selectable marker. Even more preferably, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See Lupton S. D., et al, Mol. and Cell. Biology 11:3374-3378, 1991. In addition, in preferred embodiments, the polynucleotides of the invention encoding the chimeric receptors are in retroviral vectors containing the fused gene, particularly those that confer hygromycin B resistance for positive selection in vitro, and ganciclovir sensitivity for negative selection in vivo, for example the HyTK retroviral vector described in Lupton, S. D. et al. (1991), supra. See also the publications of PCT/US91/08442 and PCT/US94/05601, by S. D. Lupton, describing the use of bifunctional selectable fusion genes derived from fusing a dominant positive selectable markers with negative selectable markers.

Preferred positive selectable markers are derived from genes selected from the group consisting of hph, nco, and gpt, and preferred negative selectable markers are derived from genes selected from the group consisting of cytosine deaminase, HSV-I TK, VZV TK, HPRT, APRT and gpt. Especially preferred markers are bifunctional selectable fusion genes wherein the positive selectable marker is derived from hph or neo, and the negative selectable marker is derived from cytosine deaminase or a TK gene or selectable marker.

A variety of methods can be employed for transducing T lymphocytes, as is well known in the art. For example, retroviral transductions can be carried out as follows: on day 1 after stimulation using REM as described herein, provide the cells with 20-30 units/ml IL-2; on day 3, replace one half of the medium with retroviral supernatant prepared according to standard methods and then supplement the cultures with 5 ug/ml polybrene and 20-30 units/ml IL-2; on day 4, wash the cells and place them in fresh culture medium supplemented with 20-30 units/ml IL-2; on day 5, repeat the exposure to retrovirus; on day 6, place the cells in selective medium (containing, e.g., an antibiotic corresponding to an antibiotic resistance gene provided in the retroviral vector) supplemented with 30 units/ml IL-2; on day 13, separate viable cells from dead cells using Ficoll Hypaque density gradient separation and then subclone the viable cells.

CD4+ and CD8+ cells can be modified with an expression vector encoding a CAR. In embodiments, these cells are then further sorted into subpopulations of naïve, central memory and effector cells as described above by sorting for cell surface antigens unique to each of those cell populations. In addition, CD4+ or CD8+ cell populations may be selected by their cytokine profile or proliferative activities. For example, CD4+ T lymphocytes that have enhanced production of cytokines such as IL-2, IL-4, IL-10, TNFα, and IFNγ as compared to sham transduced cells or transduced CD8+ cells when stimulated with antigen can be selected. In other embodiments, naïve CD4+ T cells that have enhanced production of IL-2 and/or TNFα are selected. Likewise, CD8+ cells that have enhanced IFNγ production are selected as compared to sham transduced CD8+ cells.

In embodiments, CD4+ and CD8+ cells that proliferate in response to antigen are selected. For example, CD4+ cells that proliferate vigorously when stimulated with antigen as compared to sham transduced cells, or CD8+ transduced cells are selected.

In some embodiments, CD4+ and CD8+ cells are selected that are cytotoxic for antigen bearing cells. In embodiments, CD4+ are expected to be weakly cytotoxic as compared to CD8+ cells.

The disclosure contemplates that combinations of CD4+ and CD8+ T cells will be utilized in the compositions. In one embodiment, combinations of CAR transduced CD4+ cells can be combined with CD8+ antigen reactive cells to the same antigenic specificity as the CAR. In other embodiments, CAR transduced CD8+ cells are combined with antigen reactive CD4+ cells. In yet another embodiment, CAR modified CD4+ and CD8+ cells are combined.

As described herein, the disclosure contemplates that CD4+ and CD8+ cells can be further separated into subpopulations, such as naïve, central memory, and effector cell populations. As described herein, in some embodiments, naïve CD4+ cells are CD45RO−, CD45RA+, CD62L+CD4+ T cells. In some embodiments, central memory CD4+ cells are CD62L positive and CD45RO positive. In some embodiments, effector CD4+ cells are CD62L negative and CD45RO positive. Each of these populations may be independently modified with a CAR.

As described herein, in embodiments, memory T cells are present in both CD62L+ and CD62L− subsets of CD8+ peripheral blood lymphocytes. PBMC are sorted into CD62L−CD8+ and CD62L+CD8+ fractions after staining with anti-CD8 and anti-CD62L antibodies. In some embodiments, the expression of phenotypic markers of central memory TCM include CD62L, CCR7, CD28, CD3, and CD127 and are negative for granzyme B. In some embodiments, central memory T cells are CD45RO+, CD62L+, CD8+ T cells. In some embodiments, effector $T_E$ are negative for CD62L, CCR7, CD28, and CD127, and positive for granzyme B and perforin. In some embodiments, naïve CD8+ T lymphocytes are characterized by CD8+, CD62L+, CD45RO+, CCR7+, CD28+ CD127+, and CD45RO+. Each of these populations may be independently modified with a CAR.

Each of the subpopulations of CD4+ and CD8+ cells can be combined with one another. In a specific embodiment, modified naïve CD4+ cells are combined with modified central memory CD8+ T cells to provide a synergistic cytotoxic effect on antigen bearing cells, such as tumor cells.
Methods.

The disclosure provides methods of making adoptive immunotherapy compositions and uses or methods of using these compositions for performing cellular immunotherapy in a subject having a disease or disorder.

In embodiments, a method of manufacturing the compositions comprises obtaining a modified naïve CD4+ T helper cell, wherein the modified helper T lymphocyte cell preparation comprises CD4+ T cells that have a chimeric antigen receptor comprising an extracellular antibody variable domain specific for the antigen associated with the disease or disorder and an intracellular signaling domain.

In another embodiment, a method further comprises obtaining a modified CD8+ cytotoxic T cell, wherein the modified cytotoxic T lymphocyte cell preparation comprises CD8+ cells that have a chimeric antigen receptor comprising an extracellular antibody variable domain specific for the antigen associated with the disease or disorder and an intracellular signaling domain of a T cell receptor In another embodiment, a method comprises obtaining a modified CD8+ cytotoxic T cell, wherein the modified cytotoxic T lymphocyte cell preparation comprises CD8+ T cells that have a chimeric antigen receptor comprising an extracellular antibody variable domain specific for the antigen associated with the disease or disorder and an intracellular signaling domain of a T cell receptor, and further comprising combining the modified CD8+ cytotoxic T cells with an antigen specific CD4+ helper cell lymphocyte cell preparation.

The preparation of the CD4+ and CD8+ cells that are modified with a CAR has been described above as well as in the examples. Antigen specific T lymphocytes can be obtained from a patient having the disease or disorder or can be prepared by invitro stimulation of T lymphocytes in the presence of antigen. Subpopulations of CD4+ and CD8+ T lymphocytes can also be isolated as described herein and combined in the methods of manufacturing.

The disclosure also provides methods of performing cellular immunotherapy in a subject having a disease or disorder comprising: administering a composition of any one of claims 1-19. In other embodiments, a method comprises administering to the subject a genetically modified cytotoxic T lymphocyte cell preparation that provides a cellular immune response, wherein the cytotoxic T lymphocyte cell preparation comprises CD8+ T cells that have a chimeric antigen receptor comprising an extracellular antibody variable domain specific for an antigen associated with the disease or disorder and an intracellular signaling domain of a T cell or other receptors and a genetically modified helper T lymphocyte cell preparation that elicits direct tumor recognition and augments the genetically modified cytotoxic T lymphocyte cell preparations ability to mediate a cellular immune response, wherein the helper T lymphocyte cell preparation comprises CD4+ T cells that have a chimeric antigen receptor comprising an extracellular antibody variable domain specific for the antigen associated with the disease or disorder and an intracellular signaling domain of a T cell receptor.

In another embodiment, a method of performing cellular immunotherapy in subject having a disease or disorder comprises: administering to the subject a genetically modified helper T lymphocyte cell preparation, wherein the modified helper T lymphocyte cell preparation comprises CD4+ T cells that have a chimeric antigen receptor comprising a extracellular antibody variable domain specific for an antigen associated with the disease or disorder and an intracellular signaling module of a T cell receptor. In an embodiments, the method further comprises administering to the subject a genetically modified cytotoxic T lymphocyte cell preparation, wherein the modified cytotoxic T lymphocyte cell preparation comprises CD8 positive cells that have a chimeric antigen receptor comprising a extracellular antibody variable domain specific for the antigen associated with the disease or disorder and an intracellular signaling module of a T cell receptor.

Another embodiment describes a method of performing cellular immunotherapy in a subject having a disease or disorder comprising: analyzing a biological sample of the subject for the presence of an antigen associated with the disease or disorder and administering the adoptive immunotherapy compositions described herein, wherein the chimeric antigen receptor specifically binds to the antigen.

A CAR is produced that has a component that provides for specific binding to an antigen associated with a disease or conditions, such as a solid tumor, cancer, viral infection, and an infection with a parasite. In embodiments, the intracellular signaling module of a T cell receptor of the chimeric antigen receptor comprises a transmembrane domain, a CD28 signaling domain, and a CD3 intracellular signaling domain, or other domains of T cell costimulatory molecules. In some embodiments, the intracellular signaling molecule comprises the CD3 intracellular domain, a CD28 domain, a CD28 transmembrane and signaling domain linked to a CD3 intracellular domain, or other domains of T cell costimulatory molecules.

In alternative embodiments, the T cells can be modified with a recombinant T cell receptor. TCR could be specific for any antigen, pathogen or tumor. There are TCRs for many tumor antigens in melanoma (MART1, gp100 for example), leukemia (WT1, minor histocompatibility antigens for example), breast cancer (her2, NY-BR1 for example).

In some embodiments, the CD4+ T helper lymphocyte cell is selected from the group consisting of naïve CD4+ T cells, central memory CD4+ T cells, effector memory CD4+ T cells or bulk CD4+ T cells. In a specific embodiment, CD4+ helper lymphocyte cell is a naïve CD4+ T cell, wherein the naïve CD4+ T cell comprises a CD45RO−, CD45RA+, CD62L+CD4+ T cell. In yet other embodiments, the CD8+ T cytotoxic lymphocyte cell is selected from the group consisting of naïve CD8+ T cells, central memory CD8+ T cells, effector memory CD8+ T cells or bulk CD8+ T cells. In a specific embodiment, the CD8+ cytotoxic T lymphocyte cell is a central memory T cell wherein the central memory T cell comprises a CD45RO+, CD62L+, CD8+ T cell. In a specific embodiment, the CD8+ cytotoxic T lymphocyte cell is a central memory T cell and the CD4+ helper T lymphocyte cell is a naïve CD4+ T cell.

In embodiments, the CD8+ T cell and the CD4+ T cell are both genetically modified with a CAR comprising an antibody heavy chain domain that specifically binds a pathogen or tumor-specific cell surface antigen. In other embodiments, the intracellular signaling domain of the CD8 cytotoxic T cells is the same as the intracellular signaling domain of the CD4 helper T cells. In yet other embodiments, the intracellular signaling domain of the CD8 cytotoxic T cells is different than the intracellular signaling domain of the CD4 helper T cells.

Subjects that can be treated by the present invention are, in general, human and other primate subjects, such as monkeys and apes for veterinary medicine purposes. The subjects can be male or female and can be any suitable age, including infant, juvenile, adolescent, adult, and geriatric subjects.

The methods are useful in the treatment of, for example, solid tumor, hematologic malignancy, melanoma, or infection with a virus or other pathogen. Infections with pathogens, include HIV, HCV, HBV, CMV, and parasitic disease. In some embodiments, the antigen associated with the disease or disorder is selected from the group consisting of orphan tyrosine kinase receptor ROR1, tEGFR, Her2, L1-CAM, CD19, CD20, CD22, mesothelin, CEA, and hepatitis B surface antigen.

Subjects that can be treated include subjects afflicted with cancer, including but not limited to colon, lung, liver, breast, prostate, ovarian, skin (including melanoma), bone, and brain cancer, etc. In some embodiments the tumor associated antigens are known, such as melanoma, breast cancer, squamous cell carcinoma, colon cancer, leukemia, myeloma, prostate cancer, etc. (in these embodiments memory T cells can be isolated or engineered by introducing the T cell receptor genes). In other embodiments the tumor associated proteins can be targeted with genetically modified T cells expressing an engineered immunoreceptor. Examples include but are not limited to B cell lymphoma, breast cancer, prostate cancer, and leukemia.

Subjects that can be treated also include subjects afflicted with, or at risk of developing, an infectious disease, including but not limited to viral, retroviral, bacterial, and protozoal infections, etc. Subjects that can be treated include immunodeficient patients afflicted with a viral infection, including but not limited to Cytomegalovirus (CMV), Epstein-Barr virus (EBV), adenovirus, BK polyomavirus infections in transplant patients, etc.

Cells prepared as described above can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

A treatment-effective amount of cells in the composition is at least 2 cells (for example, 1CD8+ central memory T cell and 1 CD4+ helper T cell subset) or is more typically greater than $10^2$ cells, and up to $10^6$, up to and including $10^8$ or $10^9$ cells and can be more than $10^{10}$ cells. The number of cells will depend upon the ultimate use for which the composition is intended as will the type of cells included therein. For example, if cells that are specific for a particular antigen are desired, then the population will contain greater than 70%, generally greater than 80%, 85% and 90-95% of such cells. For uses provided herein, the cells are generally in a volume of a liter or less, can be 500 mls or less, even 250 mls or 100 mls or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^9$, $10^{10}$ or $10^{11}$ cells.

In some embodiments, the lymphocytes of the invention may be used to confer immunity to individuals. By "immunity" is meant a lessening of one or more physical symptoms associated with a response to infection by a pathogen, or to a tumor, to which the lymphocyte response is directed. The amount of cells administered is usually in the range present in normal individuals with immunity to the pathogen. Thus, the cells are usually administered by infusion, with each infusion in a range of from 2 cells, up to at least $10^6$ to $10^{10}$ cells/m$^2$, preferably in the range of at least $10^7$ to $10^9$ cells/m$^2$. The clones may be administered by a single infusion, or by multiple infusions over a range of time. However, since different individuals are expected to vary in responsiveness, the type and amount of cells infused, as well as the number of infusions and the time range over which multiple infusions are given are determined by the attending physician, and can be determined by routine examination. The generation of sufficient levels of T lymphocytes (including cytotoxic T lymphocytes and/or helper T lymphocytes) is readily achievable using the rapid expansion method of the present invention, as exemplified herein. See, e.g., U.S. Pat. No. 6,040,177 to Riddell et al. at column 17.

The present invention is illustrated further in the examples sot forth below.

EXPERIMENTAL

Example 1—T Cell Transduction and Analysis of CAR Expression

A ROR1-specific CAR can be expressed in human CD8+ T cells and confers specific recognition of ROR1+ B-cell tumors and not mature normal B cells. We constructed a ROR1-specific chimeric antigen receptor that when expressed in T cells from healthy donors or CLL patients conferred specific recognition of primary B-CLL and mantle cell lymphoma.

Materials and Methods

Cell Lines

Epstein-Barr virus transformed B cells (EBV-LCL) were generated as described (25). The tumor cell lines Jeko-1, and, BALL-1, were provided by Drs Oliver Press and Jerald Radich (Fred Hutchinson Cancer Research Center). All cell lines were maintained in RPMI, 10% fetal calf serum, 0.8 mM L-glutamine, and 1% penicillin-streptomycin (LCL medium). K562 cells were obtained from the American Type Culture Collection.

Transfection of K562 Cells with ROR1

For polymerase chain reaction (PCR)-amplification of the ROR1-gene, total RNA was obtained from B-CLL cells (RNeasyPlusKit; QIAGEN) and reverse transcribed into cDNA with M-MLVReverse Transcriptase (Invitrogen). PCR was performed with specific primers

```
(ROR1-F:
5-XhoIAGAGGAGGAATGCACCGGCC-3
and

ROR1-R:
5-XhoI-CACAGAAGGTACTTGTTGCGATGT-3)
``` using Herculase-II DNA Polymerase (Stratagene). The PCR product was cloned into the MIGR-1 retroviral vector (23) and the sequence verified. Effectene transfection reagent (QIAGEN) was used to transfect Platinum-A cells (Cell Biolabs) with MIGR-1/ROR1 and produce ROR1-encoding retrovirus. K562 cells were retrovirally transduced by centrifugation at 2500 rpm for 60 minutes at 32° C., expanded, and the ROR1-positive subset was sort-purified.

Real-Time Quantitative PCR

First-strand cDNA of B-CLL, normal resting and activated B cells, and EBV-LCL was prepared as described in the previous paragraph. First-strand cDNA from normal tissues (Human Tissue panels I/II, Blood Fractions) was obtained from Clontech. Expression of ROR1 mRNA was analyzed in duplicate and normalized to GAPDH. Amplifications were performed on an ABI Prism 7900 (Applied Biosystems) in a 50 µL reaction consisting of 25 µL Power SYBR Green PCR Master Mix (Applied Biosystems), 2.5 ng of cDNA, and 300 nM gene-specific forward and reverse primers:

```
ROR1-F
5-AGCGTGCGATTCAAAGGATT-3,

ROR1-R
5-GACTGGTGCCGACGATGACT-3,

GAPDH-F
5-GAAGGTGAAGGTCGGAGTC-3,
and

GAPDH-R
5-GAAGATGGTGATGGGATTTC-3.
```

The cycle threshold (Ct) was determined using SDS software v2.2.2 (Applied Biosystems) and the level of gene expression calculated using the comparative Ct method $(2^{-\Delta\Delta Ct})$.

Vector Construction and Generation of Lentivirus

CD20-CAR(CD20R-epHIV7) and green fluorescent protein (GFP)-encoding lentiviral vectors (GFP-epHIV7) were described previously (24). The ROR1-CAR was encoded in the same vector. A mouse mAb (clone 2A2) that demonstrated specific binding to human ROR1 expressed on primary B-CLL and MCL tumor lines was generated, cloned, and characterized in a previous study. A codon-optimized nucleotide sequence encoding a scFv containing the VL and VH chain of mAb 2A2 was synthesized (GENEART) and cloned into CD20R-epHIV7 using NheI and RsrII restriction sites to replace the CD20-specific scFv. Lentivirus was produced in 293T cells cotransfected with the lentiviral vector and the packaging vectors pCHGP-2, pCMVRev2, and pCMV-G using Effectene (Qiagen). Medium was changed 16 hours after transfection and lentivirus collected after 48 hours.

Lentiviral Transduction and Isolation of CAR-Transduced Tcell Clones

PBMC from healthy donors and B-CLL patients, and sort-purified CD8+CD45RO+CD62L+ central memory T cells (TCM) were activated with anti-CD3 mAb (30 ng/mL) (25), and transduced in lentiviral supernatant supplemented with 1 µg/mL polybrene (Sigma-Aldrich) and 50 IU/mL recombinant human interleukin-2 (IL-2) on day 2 and 3 after activation by centrifugation at 2500 rpm for 60 minutes at 32° C. T cells were expanded in RPMI containing 10% human serum, 2 mM L-glutamine, and 1% penicillin streptomycin (CTL medium) (25). After expansion, an aliquot of each transduced T-cell line was stained with biotin-conjugated anti-EGFR (epithelial growth factor receptor) mAb, streptavidin-PE, and anti-CD8 mAb. EGFR+CD8+ T cells were sort purified and cloned by limiting dilution (0.5 cells/well) (25). ROR1-CAR transduced T cells were identified by staining with biotinylated recombinant Fc-ROR1 extracellular domain fusion protein and streptavidin-PE. Recombinant ROR1-protein was produced in transiently transfected 293F cells (Invitrogen), purified as described (26), and biotinylated using the BiotinTag kit (Sigma). GFP-transduced CD8+ T cells were identified by flow cytometry, sort-purified, and cloned in similar fashion.

Chromium Release and Cytokine Secretion Assays

Target cells were labeled with $^{51}$Cr (PerkinElmer) overnight, washed and incubated in triplicate at $1-2\times10^3$ cells/well with effector T cells at various effector to target (E:T) ratios. Supernatants were harvested for γ counting after a 4-hour incubation, and specific lysis was calculated using the standard formula (25).

Results

Transduced CD8+ T cells were sort-purified using a biotinylated anti-EGFR mAb and streptavidin conjugated dyes. ROR1-CAR expression on the surface of the sort-purified T cells was evaluated by staining the cells with a biotinylated recombinant Fc-ROR1 extracellular domain fusion protein that directly binds to the scFv of the ROR1-CAR, and costaining with streptavidin-conjugates. Fc-ROR1-protein specifically stained CD8+ T cells transduced with the ROR1-CAR lentiviral vector but not CD8+ T cells transduced with a control lentiviral vector encoding GFP (FIG. 1).

We established ROR1-CAR transduced (n=10) and control GFP-transduced CD8+ T-cell clones (n=4) by limiting dilution and confirmed the stable surface expression of the CAR after multiple rounds of in vitro expansion. There was no apparent difference in the growth of ROR1-CAR transduced compared with untransduced or GFP-transduced T-cell clones (data not shown).

Figure 2:
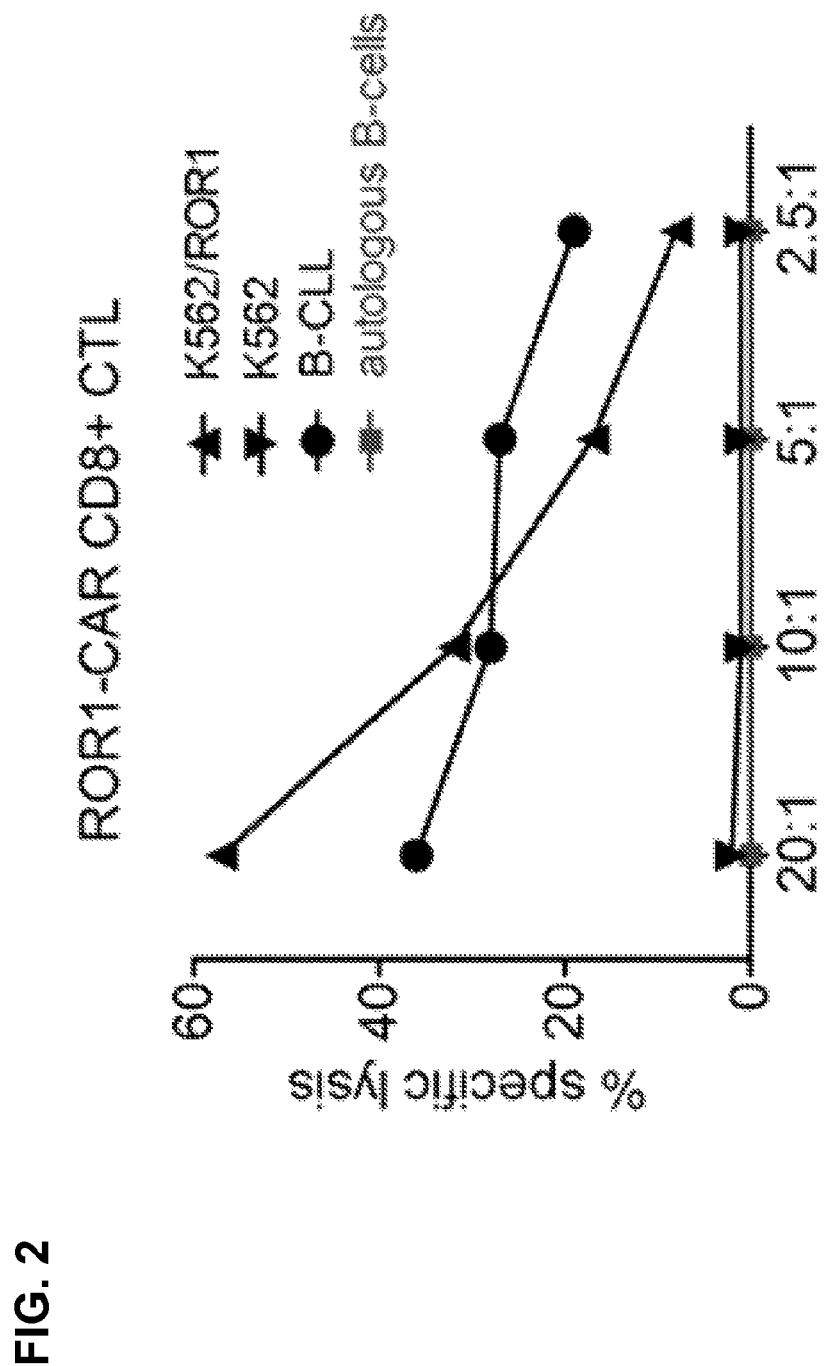
FIG. 2: shows cytolytic activity of CD8+ T cells expressing a ROR1-specific chimeric antigen receptor against a panel of human ROR1-positive tumor cell lines (K562) and primary tumor cells (B-CLL) and autologous normal B-cells in a $^{51}$Cr release assay. Consistent with the uniform expression of ROR1 on malignant but not on mature normal B cells, genetically modified CD8+ ROR1-CAR T cells only lysed ROR1+ tumor cells but not mature normal B cells. CD8+ ROR1-CAR T cells exert specific lytic activity against ROR1-positive tumor cells including primary CLL, but not against normal B cells.

The ROR1-CAR transduced T-cell clones efficiently lysed primary B-CLL and K562 cells that were stably transfected with the ROR1-gene, but not native, ROR1-negative K562 cells, demonstrating specific recognition of ROR1 (FIG. 2).

Discussion

Adoptive immunotherapies that employ CAR-modified T cells are being investigated in clinical trials for B-cell malignancies. The surface molecules that are being targeted are B-cell lineage-specific and include CD19, which is expressed on normal B-lineage cells from the pro-B-cell stage to plasma cells, and CD20, which is expressed on normal B cells from the pre-B-cell stage to memory B cells. Thus, an anticipated outcome of effective therapy targeting these molecules is depletion of normal B cells and B-cell precursors. Gene expression profiling studies have identified genes that are preferentially or exclusively expressed by malignant but not by normal B cells and ROR1 emerged as a CLL signature gene in 2 independent analyses (27,28). Specific antibodies to ROR1 developed in CLL patients after vaccination with autologous tumor cells that had been modified to express CD154 and treatment with lenalidomide without apparent toxicity to normal tissues, suggesting this tumor antigen may be a suitable target for immunotherapy (29,30).

Our studies illustrate the potential to target ROR1-positive malignant cells with engineered T cells expressing a ROR1-CAR. CD8+ ROR1-CAR T cells could be derived from both normal donors and CLL patients after lentiviral transduction of either bulk PBMCs or sort-purified TCM, that in animal models persist for extended periods after adoptive transfer (31). ROR1-CAR transduced T cells efficiently lysed primary B-CLL, but not normal resting or activated B-cells. These T cells produced effector cytokines including TNF-α, IFNγ, and IL-2, and were capable of proliferating in response to ROR1-expressing tumor cells.

Example 2—Generation of CD4+ CAR T Cell Lines and Analysis of Effector Function

CD4+ ROR1-CAR T cells can be generated from PBMC of healthy donors/CLL-patients. A ROR1-specific CAR can be expressed in human CD4+ T cells and confers specific recognition of ROR1+ B-cell tumors but not mature normal B cells.

Materials and Methods
Cell Lines

Epstein-Barr virus transformed B cells (EBV-LCL) were generated as described (25). The tumor cell lines Jeko-1, and BALL-1 were provided by Drs Oliver Press and Jerald Radich (Fred Hutchinson Cancer Research Center). All cell lines were maintained in RPMI, 10% fetal calf serum, 0.8 mM L-glutamine, and 1% penicillin-streptomycin (LCL medium). K562 and 293T cells were obtained from the American Type Culture Collection and cultured as directed.

Transfection of K562 Cells with ROR1

For polymerase chain reaction (PCR)-amplification of the ROR1-gene, total RNA was obtained from B-CLL cells (RNeasyPlusKit; QIAGEN) and reverse transcribed into cDNA with M-MLVReverse Transcriptase (Invitrogen). PCR was performed with specific primers

```
(ROR1-F:
5-XhoIAGAGGAGGAATGCACCGGCC-3
and

ROR1-R:
5-XhoI-CACAGAAGGTACTTGTTGCGATGT-3)
``` using Herculase-II DNA Polymerase (Stratagene). The PCR product was cloned into the MIGR-1 retroviral vector (23), and sequence verified. Effectene transfection reagent (QIAGEN) was used to transfect Platinum-A cells (Cell Biolabs) with MIGR-1/ROR1 and produce ROR1-encoding retrovirus. K562 cells were retrovirally transduced by centrifugation at 2500 rpm for 60 minutes at 32° C., expanded, and the ROR1-positive subset was sort-purified.

Vector Construction and Generation of Lentivirus

CD20-CAR(CD20R-epHIV7) and green fluorescent protein (GFP)-encoding lentiviral vectors (GFP-epHIV7) were described previously (24). The ROR1-CAR was encoded in the same vector. A mouse mAb (clone 2A2) that demonstrated specific binding to human ROR1 expressed on primary B-CLL and MCL tumor lines was generated, cloned, and characterized in a previous study. A codon-optimized nucleotide sequence encoding a scFv containing the VL and VI-1 chain of mAb 2A2 was synthesized (GENEART) and cloned into CD20R-epHIV7 using NheI and RsrII restriction sites to replace the CD20-specific scFv. Lentivirus was produced in 293T cells cotransfected with the lentiviral vector and the packaging vectors pCHGP-2, pCMVRev2, and pCMV-G using Effectene (Qiagen). Medium was changed 16 hours after transfection and lentivirus collected after 48 hours.

Lentiviral Transduction and Isolation of CD4+ ROR1-CAR T Cell Lines

CD4+ T cells were isolated from PBMC of healthy donors and activated with anti-CD3 mAb (30 ng/mL) (25), and transduced in lentiviral supernatant supplemented with 1 µg/mL polybrene (Sigma-Aldrich) and 50 IU/mL recombinant human interleukin-2 (IL-2) on day 2 and 3 after activation by centrifugation at 2500 rpm for 60 minutes at 32° C. T cells were expanded in RPMI containing 10% human serum, 2 mM L-glutamine, and 1% penicillin streptomycin (CTL medium).(25) After expansion, an aliquot of each transduced T-cell line was stained with biotin-conjugated anti-EGFR (epithelial growth factor receptor) mAb, streptavidin-PE, and anti-CD4 mAb. EGFR+CD4+ T cells were sort purified and expanded. ROR1-CAR transduced T cells were identified by staining with biotinylated recombinant Fc-ROR1 extracellular domain fusion protein and streptavidin-PE. Recombinant ROR1-protein was produced in transiently transfected 293 cells (Invitrogen), purified as described (26), and biotinylated using the BiotinTag kit (Sigma). GFP-transduced CD4+ T cells were identified by flow cytometry, sort-purified, and cloned in similar fashion.

Chromium Release and Cytokine Secretion Assays

Target cells were labeled with $^{51}$Cr (PerkinElmer) overnight, washed and incubated in triplicate at $1-2\times10^3$ cells/ well with effector T cells at various effector to target (E:T) ratios. Supernatants were harvested for γ counting after a 4-hour incubation, and specific lysis was calculated using the standard formula (25). For analysis of cytokine secretion, target and effector cells were plated in triplicate wells at an E/T ratio of 2:1, and interferon INFγ, tumor necrosis factor (TNF-α), and IL-2 were measured by multiplex cytokine immunoassay (Luminex) in supernatant removed after a 24-hour incubation.

CFSE Proliferation Assay

T cells were labeled with 0.2 µM carboxyfluorescein succinimidyl ester (CFSE; Invitrogen), washed, and plated with stimulator cells at a ratio of 2:1 in CTL medium containing 10 U/mL recombinant human IL-2. After a 72-hour incubation, cells were labeled with anti-CD4 mAb and propidium iodide (PI) to exclude dead cells from analysis. Samples were analyzed by flow cytometry, and cell division of live CD4+ T cells assessed by CFSE dilution.

Co-Culture Assay

ROR1-CAR transduced CD4+ T cells and ROR1-CAR transduced CD8+ cytotoxic T lymphocytes were labeled with CFSE, and co-cultured at a 2:1, 1:1 and 1:2 ratio. The co-cultures were then stimulated with K562/ROR1 cells and control K562 cells and cell proliferation measured by CFSE dye dilution assay after 5 days of incubation. For flow analysis, samples were stained with conjugated anti-CD8 and anti-CD4 mAb to distinguish CD8+ and CD4+ subsets.

Results

Figure 3:
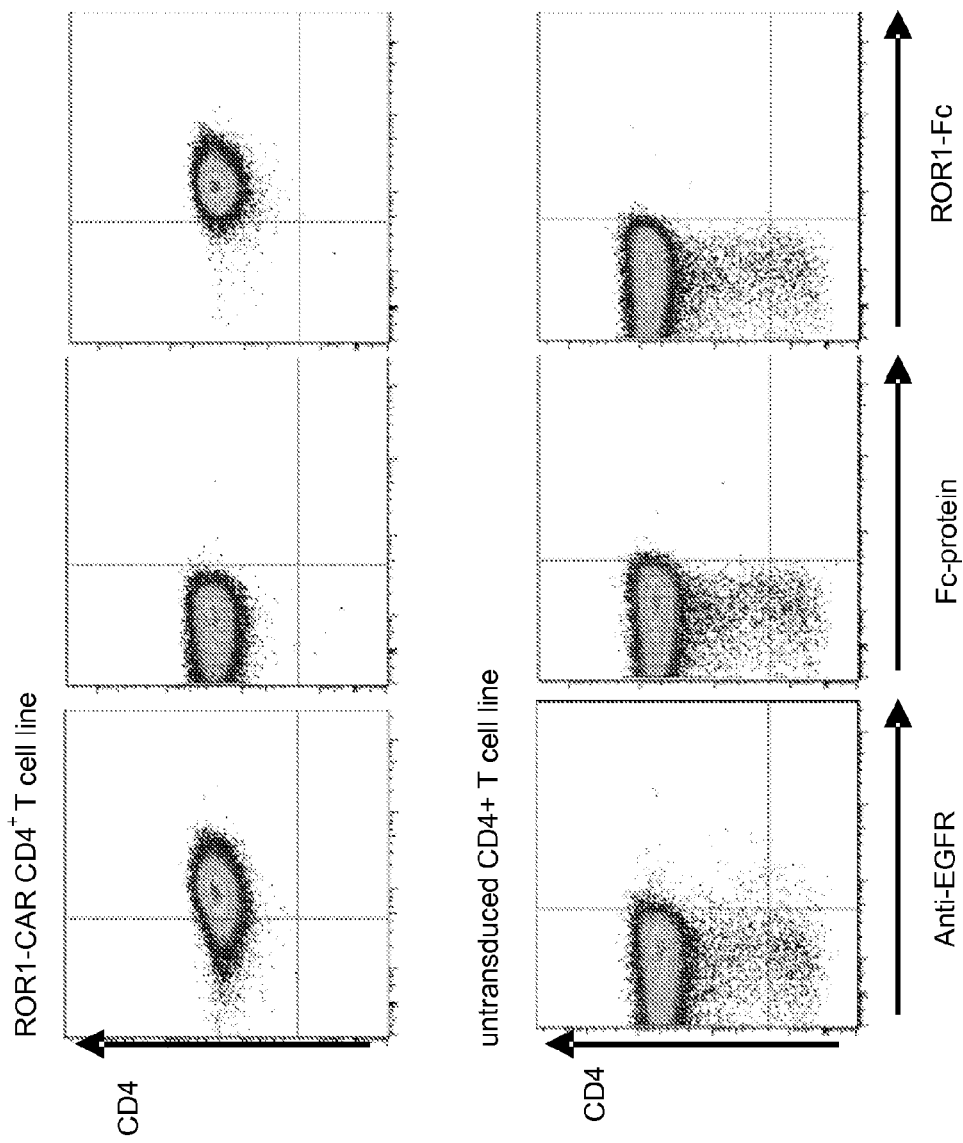
FIG. 3: shows the phenotype and CAR expression of a ROR1-CAR transduced and an untransduced CD4+ T cell line as a control. Expression of the ROR1-CAR on the cell surface of CD4+ T cells is measured by specific binding to ROR1-Fc fusion protein. Truncated Fc ROR1 fusion protein but not Fc protein alone binds directly to the ROR1-CAR and selectively stains the ROR1-CAR transduced but not the untransduced control CD4+ T cell line confirming expression of the ROR1-CAR on the cell surface and binding to ROR1-protein. Expression of the ROR1-CAR on the cell surface of CD4+ T cells is measured by specific binding to ROR1-Fc fusion protein, but not to a control Fc fusion protein.

Generation of CD4$^+$ ROR1-CAR T Cells from PBMC of Healthy Donors and CLL Patients We have shown that ROR1, an oncofetal tyrosine kinase receptor, is uniformly expressed on CLL and MCL, and developed a ROR1-CAR from an anti-ROR1 mAb that confers specific recognition of malignant, but not mature normal B cells when expressed in CD8$^+$ T cells (32). Here, we generated CD4$^+$ ROR1-CAR T cells to analyze direct tumor recognition and their ability to augment CD8$^+$ ROR1-CAR CTL. CAR-modified CD4$^+$ T cells could be readily generated from bulk peripheral CD4$^+$ T cells of healthy donors (n=4) and CLL patients (n=4) using a ROR1-CAR encoding lentiviral vector. In this vector, we encoded a truncated EGFR (epithelial growth factor receptor, tEGFR) domain downstream of the ROR1-CAR and a self-cleavable 2A element, to serve both as transduction marker and for the enrichment of transgene expressing T cells with anti-EGFR mAb (FIG. 3). We determined the frequency of CAR-modified T cells on d12 after a single transduction with ROR1-CAR encoding lentivirus (MOI=3) using the tEGFR marker and found consistently higher transduction efficiencies in CD4$^+$ compared to CD8$^+$ CAR T cell lines obtained from the same individuals. To confirm expression of the ROR1-CAR on the surface of CD4$^+$ T cells, we utilized biotinylated recombinant Fc-ROR1 extracellular domain fusion protein that directly binds to the scFv of the ROR1-CAR and specifically stained CD4$^+$ T cells transduced with ROR1-CAR lentivirus but not untransduced control CD4$^+$ T cells (FIG. 3). We enriched transgene expressing CD4$^+$ T cells using the tEGFR marker and expanded the CAR-positive T cell subset by stimulation with anti-CD3 mAb. More than 3-log expansion of CD4$^+$ CAR T cells could be achieved at the end of a 14-day stimulation cycle, which is equivalent to the amplification observed in CD8$^+$ CAR CTL. After expansion, we confirmed stable expression of the ROR1-CAR on the cell surface of CD4$^+$ CAR T cells (data not shown) and analyzed recognition of ROR1-positive tumor cells.

CD4$^+$ ROR1-CAR T Cells Specifically Recognize ROR1-Positive Tumors

Figure 4A:
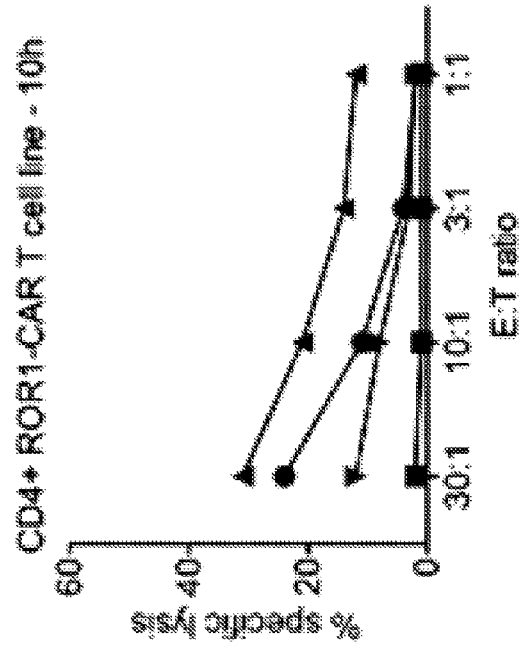
FIG. 4: (i.e., FIGS. 4A-4B, collectively) shows weak but specific cytolytic activity of CD4+ ROR1-CAR T cells in a $^{51}$Cr release assay. against a panel of ROR1-positive tumor cells including primary CLL, the mantle cell lymphoma line Jeko-1, K562 cells that were stably transfected with ROR1 (K562/ROR1), but not native ROR1-negative K562 cells. CD4+ ROR1-CAR T cells exert weak but specific lytic activity against ROR1-positive tumor cells.
Figure 4B:
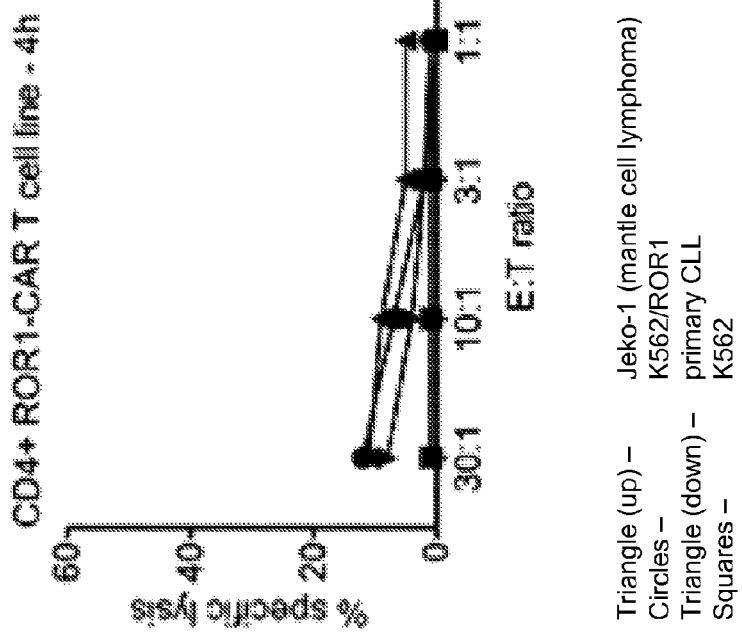
Figure 5A:
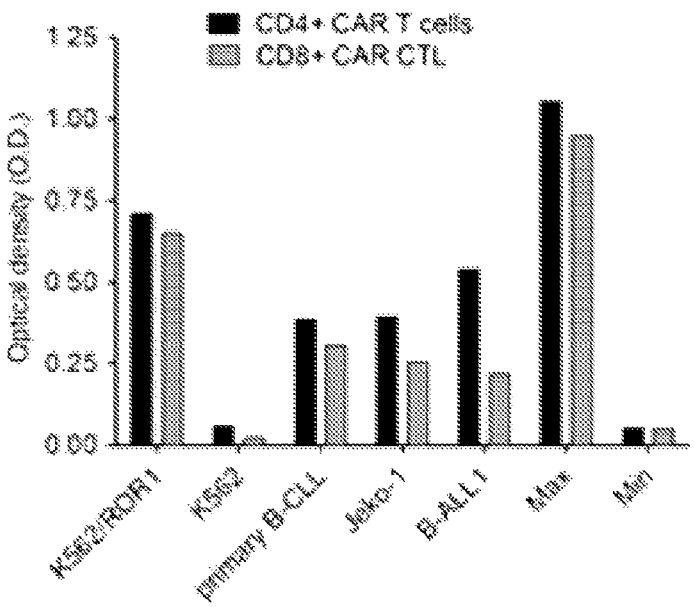
FIG. 5: (i.e., FIGS. 5A-5B, collectively) show the results from an IFNγ ELISA (FIG. 5A) and multiplex cytokine assay (FIG. 5B). Cytokine secretion of CD4+ and CD8+ ROR1-CAR T cell lines. CD4+ ROR1-CAR and CD8 ROR1-CAR T cells were co-incubated with ROR1+ tumor cells, and levels of interferon gamma (IFNg) was measured by ELISA (5A), and IFNg, TNFa, IL-2, IL-4, IL-10 and IL-17 were measured by Luminex assay (5B). CD4+ ROR1-CAR modified T cells specifically recognize ROR1-positive tumor cells and tumor cell lines and produce higher amounts of Th1 cytokines including IFN-γ, TNF-α and particularly IL-2 than CD8+ ROR1-CAR modified T cells. These data demonstrate that CD4+ ROR1-CAR T cells exert helper effector functions after stimulation through the ROR1-CAR and in addition to mediating direct anti-tumor reactivity, could also be utilized to augment the ability of CD8+ ROR1-CAR modified T cells to mediate a cellular immune response.
Figure 5B:
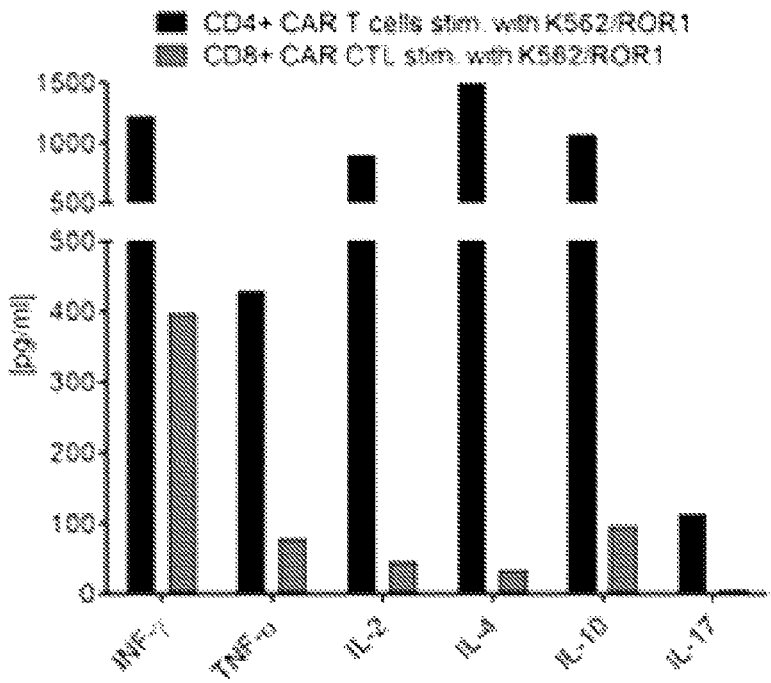

We analyzed the effector function of CD4$^+$ ROR1-CAR T cells against ROR1-positive primary tumor cells and tumor cell lines. We analyzed the ability of CD4$^+$ CAR T cells to confer direct cytotoxicity by chromium release assay (CRA) and detected weak but specific lysis of ROR1-positive target cells at the end of the standard 4-hour incubation (FIG. 4). We extended the CRA to 10 hours and observed a further increase in specific lysis, however, the overall cytolytic activity of CD4+ CAR T cells was still lower than CD8$^+$ ROR1-CAR CTL (FIG. 2, 4). CD4$^+$ ROR1-CAR T cells from both healthy donors and CLL patients specifically recognized primary CLL cells, the ROR1-positive tumor cell lines Jeko-1 (MCL) and BALL-1 (B-ALL), and K562 cells that were stably transfected with the ROR1-gene (K562/ROR1) but not native ROR1-negative K562 cells by IFN-γ ELISA, demonstrating specific recognition of ROR1 on the cell surface of target cells (FIG. 5A). Multiplex cytokine analysis revealed production of other Th1 cytokines such as TNF-α and IL-2 at significantly higher levels compared to CD8$^+$ CAR CTL, and production of IL-4, IL-10 and IL-17 (FIG. 5B).

Figure 6:
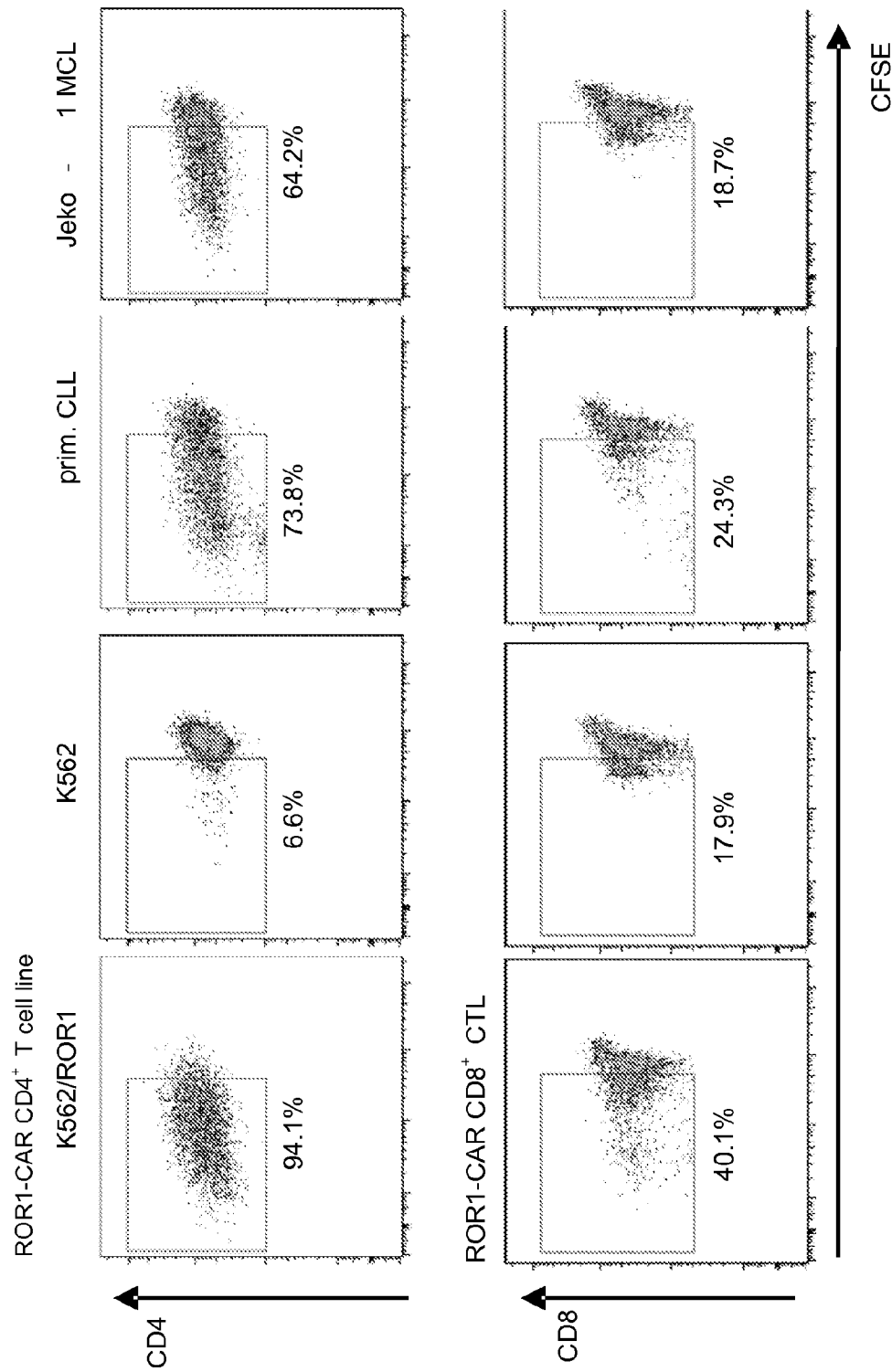
FIG. 6 depicts the results of a proliferation study showing that CD4+ ROR1-CAR T cells are induced to proliferate after stimulation with ROR1-positive tumor cell lines and primary tumor cells (CFSE assay) and that both the percentage of proliferating cells and number of cell divisions that the proliferating subset underwent were significantly higher compared to CD8+ ROR1-CAR modified T cells. CD4+ ROR1-CAR T cells proliferate more vigorously after stimulation with ROR1-positive tumor cells (K562/ROR1, primary CLL, and Jeko MCL) compared to CD8+ ROR1-CAR CTLs.

Next, we evaluated the proliferation of CD4$^+$ CAR T cells after stimulation with ROR1-positive tumor cells by CFSE staining and used stringent culture conditions without addition of exogenous cytokines to remove any potential unspecific stimulus. CD4$^+$ CAR T cells showed dramatic and specific proliferation in response to ROR1-positive tumor cells. Both the percentage of T cells that was induced to proliferate and the number of cell divisions that the proliferating subset performed was significantly higher in CD4$^+$ compared to CD8$^+$ CAR T cells (FIG. 6). Collectively, our data demonstrate that CD4$^+$ T cells obtained from both healthy donors and CLL patients acquire anti-tumor reactivity after genetic modification with a ROR1-specific CAR. Moreover, the ability to proliferate in the absence of exogenous cytokines and to produce high levels of Th1 cytokines suggest that CD4$^+$ CAR T cells exert typical helper functions after stimulation through the CAR and in addition to conferring direct anti-tumor effects, could also be utilized to augment CD8$^+$ CAR CTL.

Figure 7:
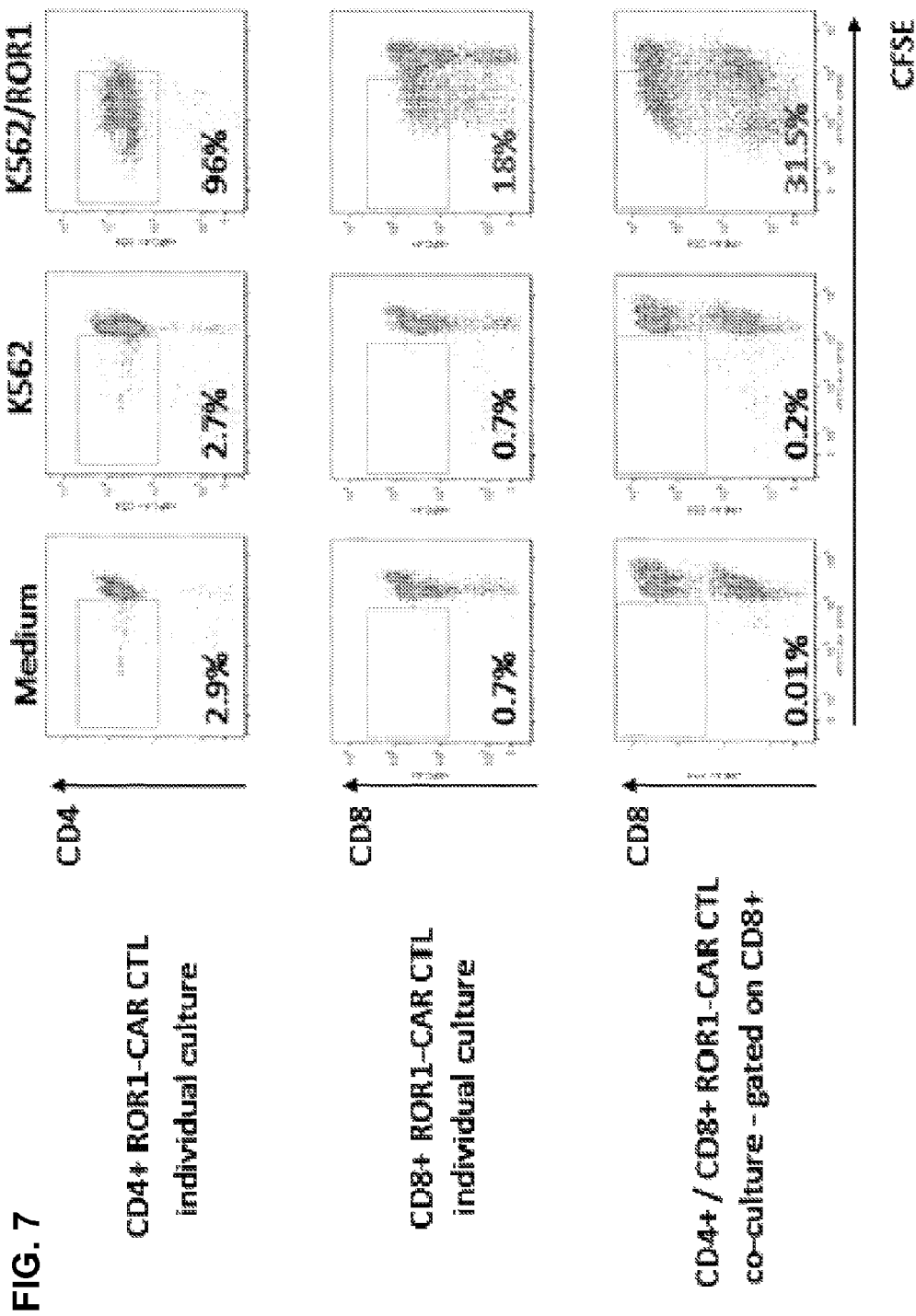
FIG. 7: Polyclonal unselected CD4+ ROR1 CAR T cells provide help to CD8+ ROR1-CAR CTLs by promoting their proliferation in response to tumor. CD4+ ROR1-CAR T cells (derived from bulk CD4+ T cells) significantly increased proliferation of polyclonal unselected CD8+ ROR1-CAR CTLs (18% in individual culture→31.5% after co-culture with CD4+ CAR T cells).

CAR-Modified, but not Untransduced CD4$^+$ T Cells Provide Help to CD8$^+$ CAR CTL To analyze whether CD4$^+$ CAR T cells are able to provide help to CD8$^+$ CAR CTL, we performed co-culture experiments with CAR-transduced and control untransduced polyclonal CD4$^+$ and CD8$^+$ T cell lines that we established from healthy donors and CLL patients. As readout for provision of help, we defined an improvement in tumor-specific CDC effector function in the presence of CD4$^+$ T cells compared to CD8$^+$ T cells cultured alone. We combined either CAR-transduced or untransduced control CD4$^+$ T cells with CD8$^+$ CAR CTL at distinct CD4:CD8 ratios (2:1, 1:1, 1:2), stimulated them with ROR1-positive tumor cells and measured proliferation by CFSE dye dilution. We found, that the addition of CAR-transduced, but not untransduced CD4$^+$ T cells to CD8$^+$ CAR CTL significantly increased specific proliferation of the CD8$^+$ subset compared to CD8$^+$ CAR CTL alone (FIG. 7). The increase in proliferation was most pronounced, when at least an equivalent amount of CD4$^+$ CAR T cells (CD4:CD8 ratio of 2:1 or 1:1) was added to the co-culture. The combination of untransduced CD4$^+$ with untransduced CD8$^+$ T cells served as additional control and did not induce unspecific proliferation in the CD8$^+$ subset (data not shown).

Discussion

Gene expression profiling studies have identified genes that are preferentially or exclusively expressed by malignant but not by normal B cells and ROR1 emerged as a CLL signature gene in 2 independent analyses (27,28). Our studies illustrate the potential to target ROR1-positive malignant cells with engineered T cells expressing a ROR1-CAR. CD8 and CD4+ ROR1-CAR T cells could be derived from normal donors after lentiviral transduction of either bulk PBMCs or sort-purified T cells. CD8+ ROR1-CAR transduced T cells efficiently lysed primary B-CLL, but not normal resting or activated B-cells. CD4+ ROR1-CAR transduced T cells weakly lysed primary B-CLL, but not normal resting or activated B-cells. These T cells produced effector cytokines including TNF-α, IFNγ, IL-2, IL-4, and IL-10. CAR-transduced CD4+ T cells produced significantly higher amounts of cytokines than the transduced CD8+ cells. Both cell types were capable of proliferating in response to ROR1-expressing tumor cells. Again, CD4+ ROR1-CAR T cells proliferated 2-3 fold higher than CD8+ ROR1-CAR CTLs. These results indicate that the transduced CD4+ helper T cells exert typical helper functions suggesting they could be utilized to augment CD8+ CAR CTLs.

Figure 8A:
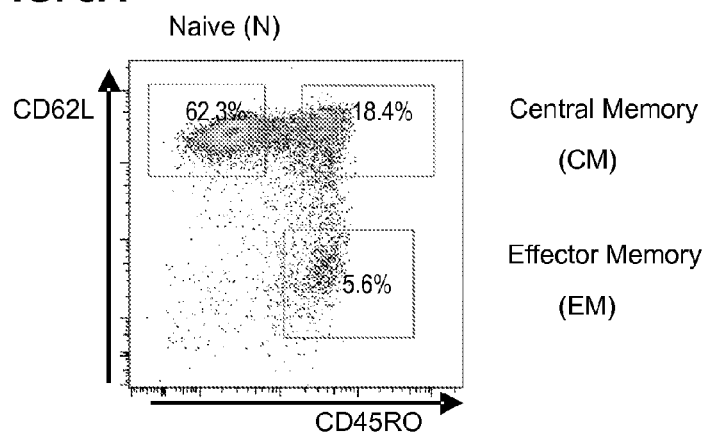
FIG. 8A shows flow sort purification of naïve, central and effector memory CD4+ T cells based on expression of CD45RA, CD45RO, CD62L.

Example 3—The Effector Function of CD4+ ROR1-CAR T Cells from Derived from Naïve, Central and Effector Memory Subsets The effector function of CD4 T cells derived from naïve, central and effector memory subsets and then modified with the ROR1 CAR were compared.
Materials and Methods
Sort Purification of Naïve, Central, and Effector Memory CD4 Cells CD4+ T cells were isolated from PBMC of a healthy donor using negative magnetic bead selection (Miltenyi CD4 isolation kit) that yields untouched CD4+ T cells. The CD4+ fraction was labeled with conjugated anti-CD45RA, anti-CD45RO and anti-CD62L mAb and flow sort purified using a FACS Aria flow sorter (BD Biosciences), and naïve (CD45RA+CD45RO−CD62L+), central memory (CD45RA−CD45RO+CD62L+) and effector memory (CD45RA−CD45RO+CD62L−) CD4+ T cells purified based on expression of these defined markers.
CFSE Proliferation Assay T cells were labeled with 0.2 μM carboxyfluorescein succinimidyl ester (CFSE; Invitrogen), washed, and plated with stimulator cells at a ratio of 2:1 in CTL medium containing 10 U/mL recombinant human IL-2. After a 72-hour incubation, cells were labeled with anti-CD8 or CD4 mAb and propidium iodide (PI) to exclude dead cells from analysis. Samples were analyzed by flow cytometry, and cell division of live CD8+ and CD4+ T cells assessed by CFSE dilution.
Cytokine Assays For analyses of cytokine secretion, target and effector cells were plated in triplicate wells at an E/T ratio of 2:1, and interferon INFγ, tumor necrosis factor (TNF-α), and IL-2 were measured by multiplex cytokine immunoassay (Luminex) in supernatant removed after a 24-hour incubation.
Results We flow sort purified CD4+ N, central (CM) and effector memory (EM) CD4+ T cells from the peripheral blood of 3 healthy donors based on expression of CD45RA, CD45RO and CD62L (FIG. 8A), and compared their effector function after modification with the ROR1-CAR. We achieved similarly high transduction efficiencies in CAR T cell lines derived from each of the three subsets. Multiparameter flow cytometry after enrichment of transgene expressing T cells showed expression of CD45RO and loss of CD45RA in the CD4+ N CAR T cell line, consistent with an activated phenotype after the lentiviral transduction. The CD4+ N, CM and EM CAR T cell lines retained differential expression of CD62L, confirming that the initial flow sort purification had been performed with high purity.

Figure 8B:
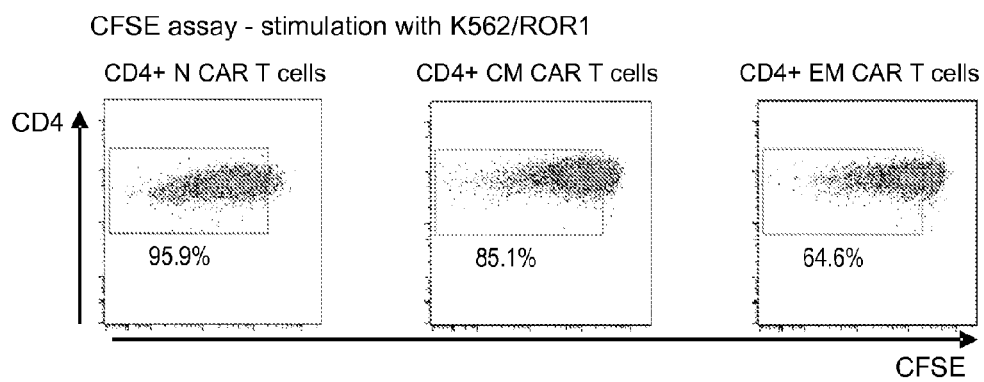
FIG. 8B shows analysis of proliferation of ROR1-CAR T cell lines that were derived by lentiviral transduction of sort purified naïve, central and effector memory CD4+ T cells (CFSE assay).
Figure 8C:
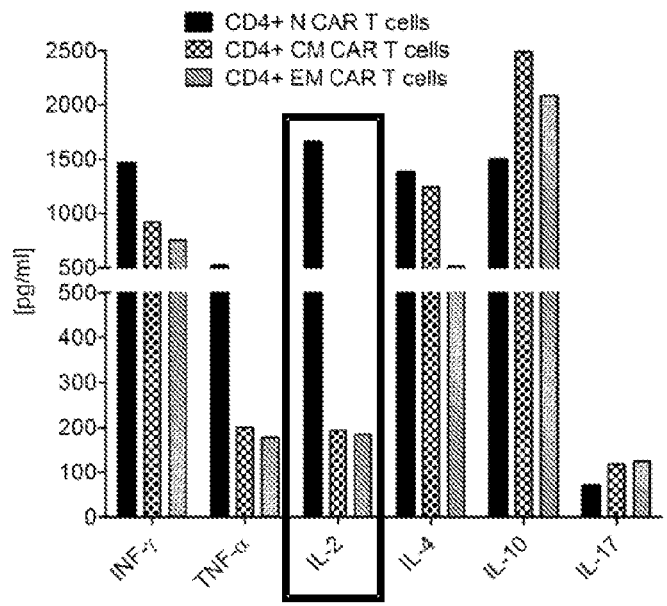
FIG. 8C shows analysis of cytokine secretion of ROR1-CAR T cell lines from sort purified naïve, central and effector memory CD4+ T cells (Luminex assay).
Figure 8D:
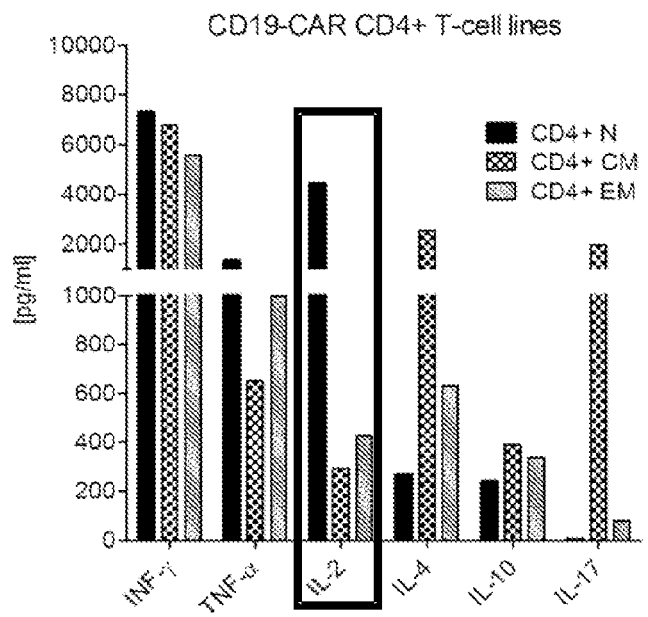
FIG. 8D shows analysis of cytokine secretion of CD19-CAR T-cell lines from sort purified naïve, central and effector memory CD4+ T cells (Luminex assay). The cytokine profile obtained by multiplex cytokine analysis (FIG. 8B) and proliferative capacity by CFSE staining (FIG. 8C) shows that CD4+ ROR1-CAR modified T cells derived from the naïve subset produced the highest levels of Th1 cytokines and proliferated most vigorously after stimulation with ROR1-positive tumor cells, suggesting they may be best suited to augment CD8+ ROR1-CAR CTLs. Analysis of cytokine secretion of CD19-CAR T cell lines from sort-purified naïve, central and effector memory CD4+ T cells (Luminex assay), demonstrates that the activity of CD4 T cell subsets is generalizable to many CARs.

Then, we analyzed tumor recognition, cytokine secretion and proliferation of CD4+ CAR T cells derived from N, CM and EM subsets and compared them to the CAR T cell lines generated from bulk CD4+ T cells. We observed specific recognition of ROR1-positive tumor cells by IFN-γ ELISA in each of the cell lines. Multiplex cytokine analysis revealed that CD4+ CAR T cells derived from the N subset produced by far the highest levels of Th1 cytokines, especially IL-2 (FIG. 8C) and CFSE dye dilution showed they proliferated most vigorously in response to stimulation with ROR1-positive tumor cells (FIG. 8B).
Discussion Our studies illustrate the potential to target ROR1-positive malignant cells with engineered T cells expressing a ROR1-CAR. CD8 and CD4+ ROR1-CAR T cells could be derived from both normal donors after lentiviral transduction of either bulk PBMCs and sort-purified T cells from defined naïve or memory T cell subsets. CD4+ naïve, central memory, and effector T cells produced effector cytokines including TNFα, IFNγ, IL-2, IL-4, and IL-10. CAR-transduced CD4+ cells derived from the naïve subset produced significantly higher amounts of TNFα and IL-2 than central and effector memory derived CD4+ CAR T cells after signaling through the CAR. All CD4 cell types were capable of proliferating in response to ROR1/K562, however in the CAR-transduced CD4+ cells derived from the naïve subset, the percentage of T cells that was induced to proliferate and the number of cell divisions that the proliferating subset underwent were significantly higher. Both cytokine profile and proliferative capacity indicate that naïve CD4+ ROR1-CAR T cells may be best suited to augment CD8+ ROR1-CAR CTL.

Example 4—Naive CD4+ T Cells are Better Helpers than Memory CD4+ T Cells

Figure 9:
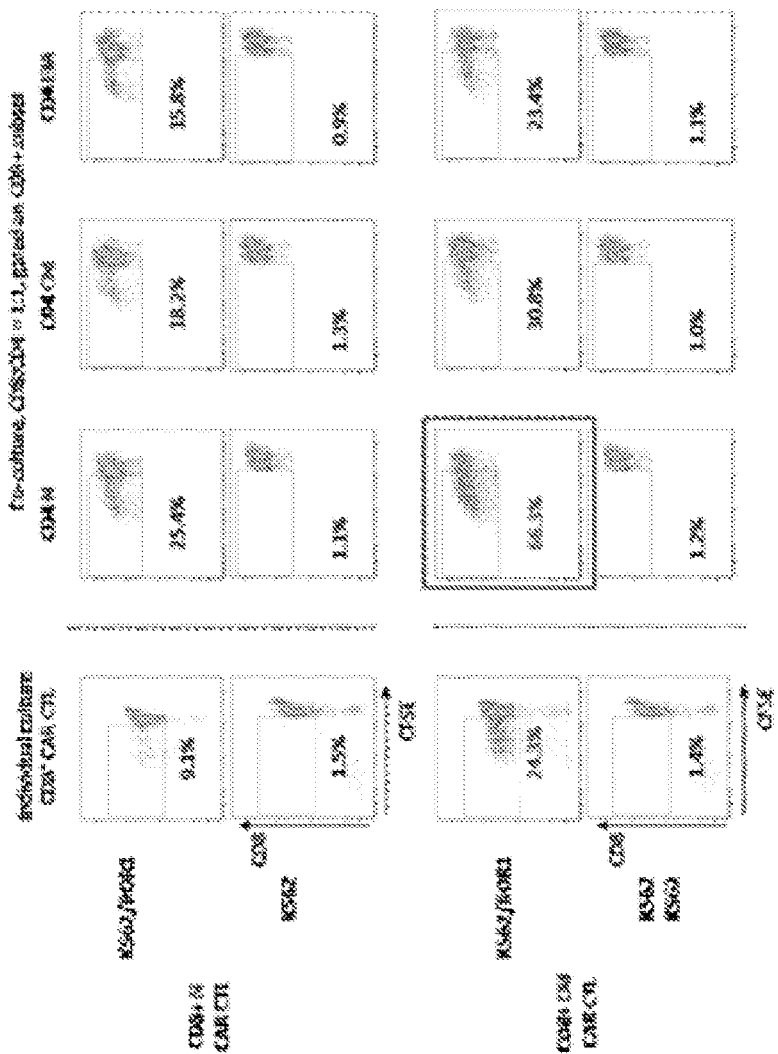
FIG. 9: shows co-culture of CD8+ ROR1-CAR modified T cells with CD4+ROR1-CAR modified T cells (but not untransduced control CD4+ T cells). Co-culture of CD8+ ROR1-CAR CTLs and CD4+ ROR1-CAR T cell lines derived from naïve, central and effector memory subsets to define the optimal combination of CD8+ and CD4+ T cells that would allow maximum proliferation of CD8+ ROR1-CAR CTLs. CD4 naïve ROR1-CAR T cells provide the greatest proliferation of CD8 central memory ROR1-CAR CTLs. Co culture leads to an increase in tumor-specific proliferation of the CD8+ subset, and that maximum proliferation of the CD8+ subset is observed after co-culture with CD4+ ROR1-CAR T cells derived from naïve CD4+ T cells, demonstrating that naïve

Naïve, central memory, and effector transduced CD4+ T cells were cocultured with transduced CD8+ cytotoxic T lymphocytes and the proliferative response of the cells was measured in response to stimulation with K562/ROR1 cells.
Materials and Methods
Co-Culture Naïve, central and effector memory derived ROR1-CAR transduced CD4+ T cells and ROR1-CAR transduced CD8+ cytotoxic T lymphocytes derived from naïve and central memory CD8+ T cells were labeled with CFSE, and CD4+ and CD8+ CAR T cell lines co-cultured at a 1:1 ratio. The co-cultures were then stimulated with K562/ROR1 cells and control K562 cells and cell proliferation was measured by CFSE dye dilution assay after 5 days of incubation. For flow analysis, samples were stained with conjugated anti-CD8 and anti-CD4 mAb to distinguish CD8+ and CD4+ subsets.
Results
CD4+ Naïve CAR T Cells have a Superior Ability to Augment the Effector Function of CD8+ CAR CTL We compared the helper function of CD4+ N, CM and EM CAR T cell lines to determine whether the favorable cytokine profile and proliferative potential of CD4+ N CAR T cells would also translate into the strongest helper effect for CD8+ CAR CTL. Previous work has demonstrated that there are intrinsic differences between N, CM and EM CD8+ T cells that affect their potential utility for adoptive immunotherapy. Our group has recently shown that CM but not EM derived CD8+ T cells are able to persist for extended periods after adoptive transfer which makes them a preferred subset of CD8+ T cells for immunotherapy (33,34). Other groups suggested that CD8+ N T cells may also possess favorable traits for use in T cell therapy (35,36). Thus, we generated CD8+ CAR CTLs from sort purified N and CM T cells to determine the optimal combination of CDC and CD4+ CAR T cell subsets. Following lentiviral transduction and enrichment of CAR-transduced CD8+ T cells using the tEGFR marker, we confirmed tumor-reactivity of the CD8+ N, and CM CAR CTLs (data not shown) and performed co-culture experiments with CD4+ CAR T cells as before. As anticipated, co-culture of CD8+ N and CM CAR CTL with CD4+ N CAR T cells resulted in significantly higher tumor-specific proliferation of the CD8+ subset compared to co-culture with CD4+ CM or EM CAR T cells, or the CD8+ CAR CTL alone (FIG. 9). Out of all combinations, maximum proliferation of the CD8+ CAR CTL in response to stimulation with ROR1-positive tumor cells was observed after co-culture of CD4+ N CAR T cells with CD8+ CM CAR CTL (FIG. 9). Collectively, our data demonstrate that there are intrinsic differences between N, CM and EM CD4+ T cells in their cytokine profile and proliferative potential, with higher production of IL-2 and superior proliferation in CD4+ N T cells. Our data suggest that sort purified N, rather than CM, EM or bulk CD4+ T cells may be best suited to augment the effector function of CD8+ CTL, and complement previous work in CD8+ T cells that CM derived CD8+ T cells possess favorable characteristics for use in adoptive immunotherapy.

Discussion

Collectively, these data demonstrate that the adoptive transfer of ROR1-CAR modified CD4+ and CD8+ T cells confers potent anti-tumor responses in an in vivo model of aggressive systemic lymphoma and provide evidence for a beneficial and synergistic effect of CD4+ CAR T cells on the anti-tumor efficacy of CD8+ CAR CTL. Our data illustrate how the analysis of cell-intrinsic qualities can inform the rational design of cell products containing both tumor-specific CD8+ and CD4+ T cells to improve outcomes of cancer immunotherapy.

Example 5—Mouse Tumor Model of Systemic Mantle Cell Lymphoma (NSG/Jeko-1-ffLuc)

We examined the effect of providing CD4 help on the anti-tumor efficacy of ROR1-CAR modified CD8+ CTL in an in vivo model of aggressive systemic mantle cell lymphoma.

Materials and Methods

Sublethally irradiated NOD/SCID/gamma$^{-/-}$ (NSG) mice were engrafted via tail vein injection with $5 \times 10^5$ Jeko-1 cells that had been stably transfected with firefly luciferase (Jeko-1/ffLuc) to enable assessment of tumor burden and distribution using bioluminescence imaging. We confirmed the consistent engraftment (take rate=100%) and development of rapidly progressive disseminated lymphoma in NSG mice under these conditions. Following tumor engraftment, groups of 3 mice received either CD8+ CAR CTLs (group 1), CD4+ CAR T cells (group 2), a combination of CD8+ and CD4+ ROR1-CAR transduced T cells (group 3), untransduced control T cells (group 4, 5, 6) via tail vein injection or no treatment (group 7). The total number of transferred T cells was $10 \times 10^6$ in all cases. We obtained eye bleeds from the mice 2 days after adoptive transfer and confirmed the presence of ROR1-CAR transduced or untransduced T cells in the peripheral blood.

Results

Figure 10:
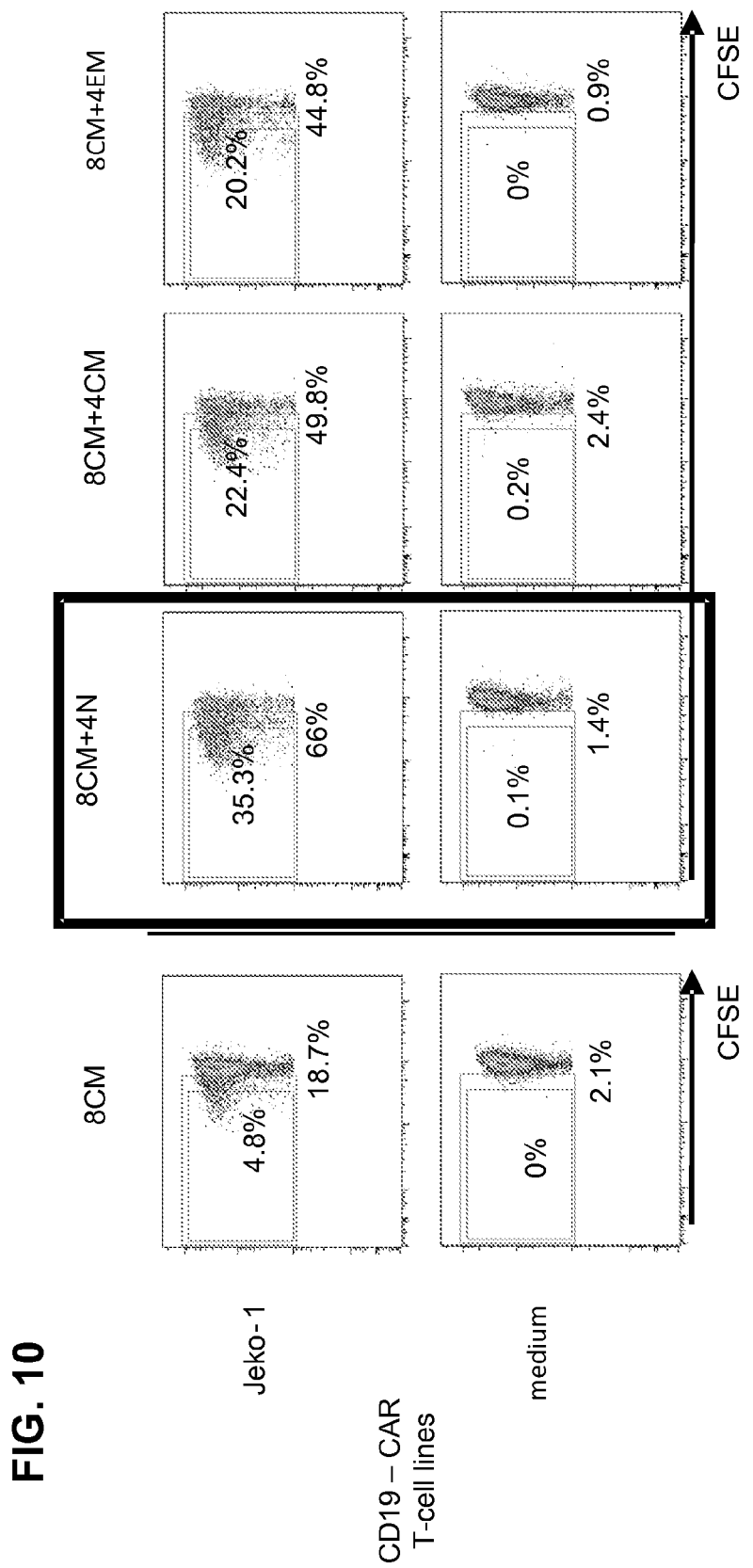
FIG. 10: shows the superior ability of CD4+ CAR T-cell lines derived from the naïve subset to augment tumor-specific proliferation of central memory-derived CD8+ CAR CTL in co-culture experiments with CD8+ CD19-CAR CTLs and CD4+ CD19-CAR T-cell lines, stimulated with the CD19+ mantle cell lymphoma tumor line Jeko-1. The superior ability of CD4+ CAR T-cell lines derived from the naïve subset to augment tumor-specific proliferation of central memory-derived CD8+ CAR CTL was confirmed in co-culture experiments with CD8+ CD19-CAR CTLs and CD4+ CD19-CAR T-cell lines, stimulated with the CD19+ mantle cell lymphoma tumor line Jeko-1.

On day 6 after T-cell transfer, we performed bioluminescence imaging to evaluate tumor burden. The strongest anti-tumor effect was observed in mice that received the combination of CD8+ and CD4+ ROR1-CAR T cells, with >2 log reduction in bioluminescence signal compared to the control group (FIG. 10). We also observed a strong anti-tumor effect in mice that received either CD8+ or CD4+ ROR1-CAR modified T cells, with >1 log reduction in bioluminescence signal compared to controls (FIG. 10). Importantly, the reduction in tumor burden after administration of the CD8+/CD4+ CAR T cell combination was greater than that of the CD8+ CAR CTL and CD4+ CAR T cell groups combined suggesting that CD4+ CAR T cells and CD8+ CAR CTL were working synergistically.

Discussion

Collectively, these data demonstrate that the adoptive transfer of ROR1-CAR modified CD4+ and CD8+ T cells confers potent anti-tumor responses in an in vivo model of aggressive systemic lymphoma and provide evidence for a beneficial and synergistic effect of CD4+ CAR T cells on the anti-tumor efficacy of CD8+ CAR CTL. Our data illustrate how the analysis of cell-intrinsic qualities can inform the rational design of cell products containing both tumor-specific CD8+ and CD4+ T cells to improve outcomes of cancer immunotherapy.

Example 6—CD19 CAR T Cells Exhibit the Same Synergy

We examined the effect of providing CD4 help on the anti-tumor efficacy of CD19 modified CD8+ CTL in coculture in vitro and in an in vivo model of aggressive systemic mantle cell lymphoma.

Materials and Methods

CD19 CAR T cells can be prepared as described in US 2008/0131415, which is hereby incorporated by reference.

Co-Culture Assay

CD19-CAR transduced CD4+ T cells and CD19-CAR transduced CD8+ cytotoxic T lymphocytes were labeled with CFSE, and co-cultured at a 2:1, 1:1 and 1:2 ratio. The co-cultures were then stimulated with K562/ROR1 cells and control K562 cells and cell proliferation measured by CFSE dye dilution assay after 5 days of incubation. For flow analysis, samples were stained with conjugated anti-CD8 and anti-CD4 mAb to distinguish CD8+ and CD4+ subsets.

In Vivo Model

Sublethally irradiated NOD/SCID/gamma$^{-/-}$ (NSG) mice were engrafted via tail vein injection with $5 \times 10^5$ Jeko-1 cells that had been stably transfected with firefly luciferase (Jeko-1/ffLuc) to enable assessment of tumor burden and distribution using bioluminescence imaging. We confirmed the consistent engraftment (take rate=100%) and development of rapidly progressive disseminated lymphoma in NSG mice under these conditions. Following tumor engraftment, groups of 3 mice received either CD8+ CD19 CAR CTLs (group 1), CD4+ CD 19 CAR T cells (group 2), a combination of CD8+ and CD4+ CD19CAR transduced T cells (group 3), untransduced control T cells (group 4, 5, 6) via tail vein injection or no treatment (group 7). The total number of transferred T cells was $10 \times 10^6$ in all cases. We obtained eye bleeds from the mice 2 days after adoptive transfer.

Results

FIG. 10 shows the superior ability of CD4+ CAR T-cell lines derived from the naïve subset to augment tumor-specific proliferation of central memory-derived CD8+ CAR CTL in co-culture experiments with CD8+ CD19-CAR CTLs and CD4+ CD19-CAR T-cell lines, stimulated with the CD19+ mantle cell lymphoma tumor line Jeko-1. Although, CD4+ CAR T-cell lines derived from the central or effector memory subset augment tumor-specific proliferation of central memory-derived CD8+ CAR CTL to much less extent.

Figure 11A:
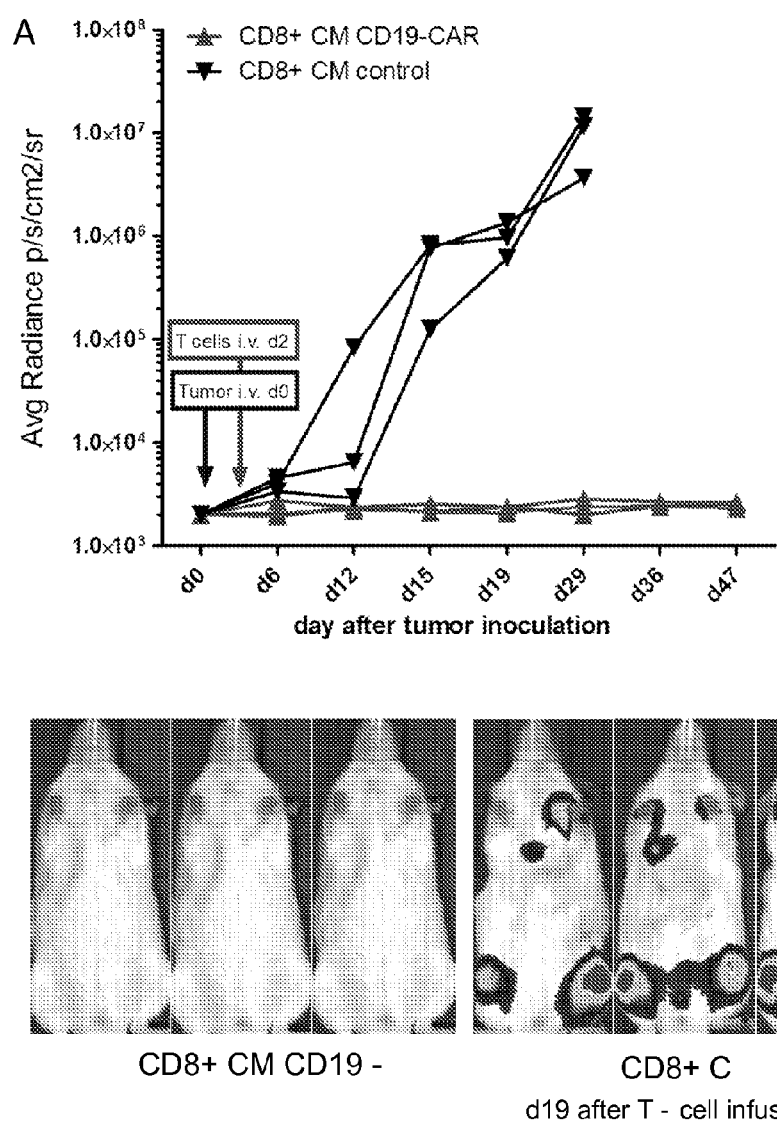
FIG. 11: shows that CD8+ CAR T cells and CD4+ CAR T cells independently confer direct anti-tumor efficacy in a lymphoma model in immunodeficient mice (NOD/SCID-Raji). Groups of mice (n=3) were inoculated with firefly-luciferase expressing Raji tumor cells via tail vein injection and treated with a single dose of 10×10^6 T cells. Mice received either CD19-CAR transduced or control mock-transduced CD8+ central memory-derived (A), or CD19-CAR transduced or control mock-transduced CD4+ naïve-derived T cells (B). Tumor burden and distribution was analyzed using serial bioluminescence imaging.
Figure 11B:
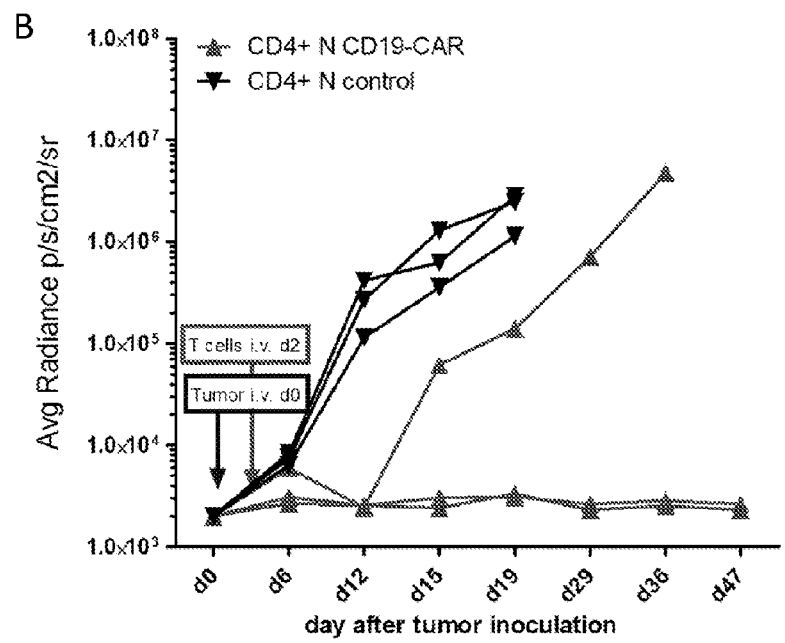
Figure 11B:
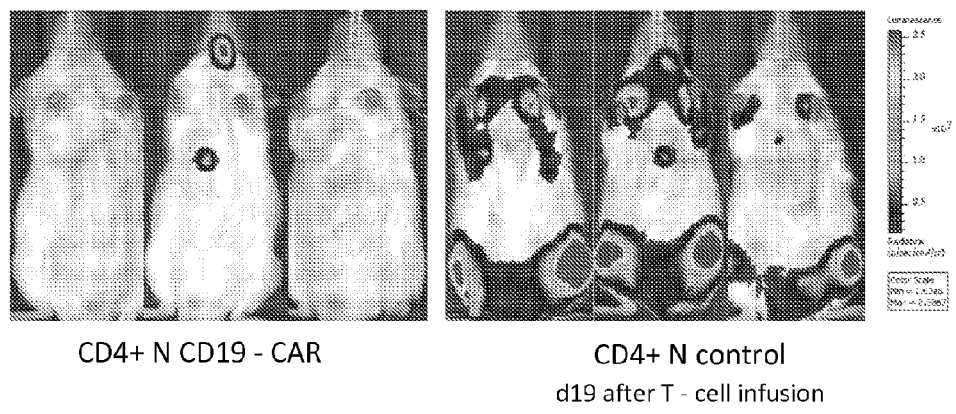

FIG. 11 shows that CD8+ CAR T cells and CD4+ CAR T cells independently confer direct anti-tumor efficacy in a lymphoma model in immunodeficient mice (NOD/SCID-Raji). Mice received either CD19-CAR transduced or control mock-transduced CD8+ central memory-derived (A), or CD19-CAR transduced or control mock-transduced CD4+ naïve-derived T cells (B).

Figure 12:
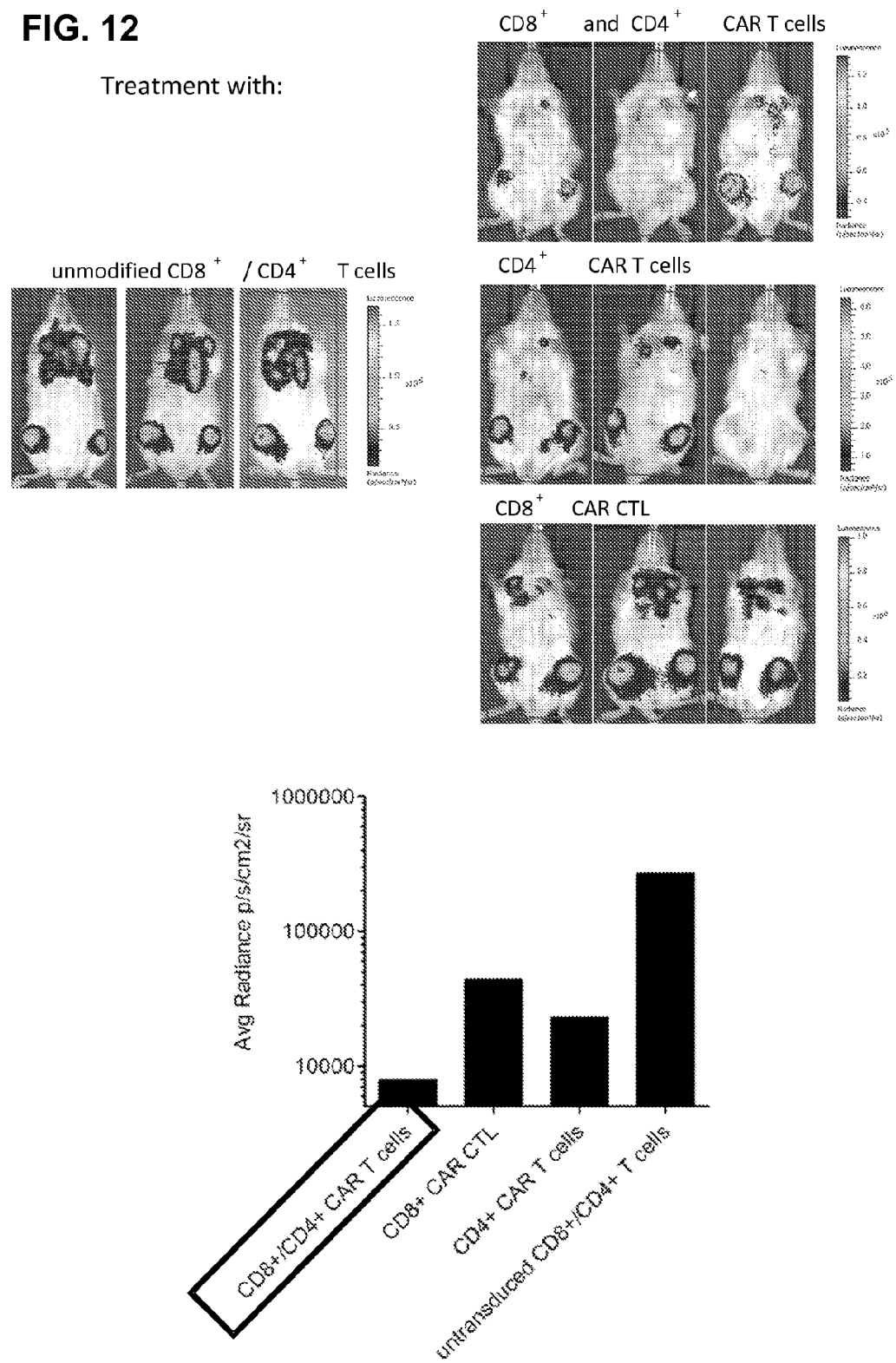
FIG. 12: shows the augmentation and synergistic effect CD4+ ROR1-CAR modified T cells on the anti-tumor efficacy of CD8+ ROR1-CAR CTLs in a mouse tumor model of systemic mantle cell lymphoma (NSG/Jeko-1-ffLuc). Anti-tumor efficacy of ROR1-CAR modified CD8+ and CD4+ T cells in a mouse tumor model of systemic aggressive mantle cell lymphoma (NSG/Jeko-1). Analysis of tumor burden using bioluminescence imaging after adoptive transfer of CD8+ ROR1-CAR CTLs, CD4+ ROR1-CAR T cells or a combination of CD8+ and CD4+ ROR1-CAR T cells T cells. All mice received the same total dose of CAR T cells.
Figure 13A:
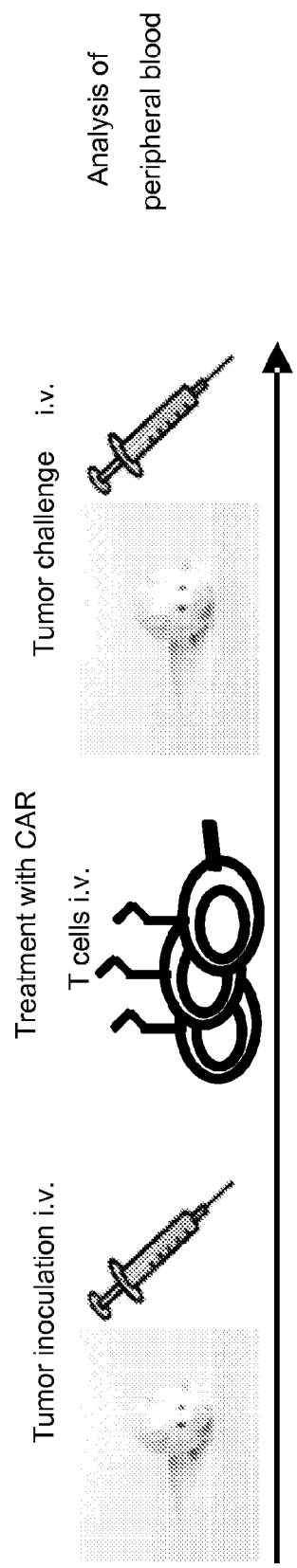
FIG. 13: shows synergy of CD8+ and CD4+ CD19-CAR T cells in a mouse model of systemic lymphoma (NSG/Raji). NSG mice were inoculated with firefly-luciferase transduced Raji tumor cells. Engraftment of the Raji tumor was confirmed by bioluminescence imaging on day 6 after tumor inoculation (before treatment) (treatment scheme shown in A, tumor engraftment by bioluminescence shown in B). Groups of mice (n=5) were then treated with either CD8+ CD19-CAR modified T cells, or a combined T-cell product that contained both CD8+ and CD4+ CD19-CAR T cells. All mice received the same total dose of T cells (10×10^6). Analysis of tumor burden using bioluminescence imaging showed complete eradication of the Raji tumors in the cohorts of mice treated with CD8+ CD19-CAR T cells, and in mice treated with the combined CD8+ and CD4+ CD19-CAR T-cell product (after treatment middle black and grey bars) B). The mice were then challenged with a second inoculum of Raji tumor cells and the frequency of CD4+ and CD8+ CAR T cells in the peripheral blood, and tumor engraftment were analyzed. In mice treated with a combined CD8+ and CD4+ CAR T-cell product, significantly higher levels CD8+ CAR T cells after the tumor challenge (C lower panels), and complete rejection of the Raji inoculum (after tumor challenge right grey bar, B). In contrast, in mice that had received CD8+ CD19-CAR CTL alone, we did not detect an increase in CAR T cells after the tumor challenge (C) and the Raji tumor cells were able to engraft (after tumor challenge right black bar, panel B).
Figure 13B:
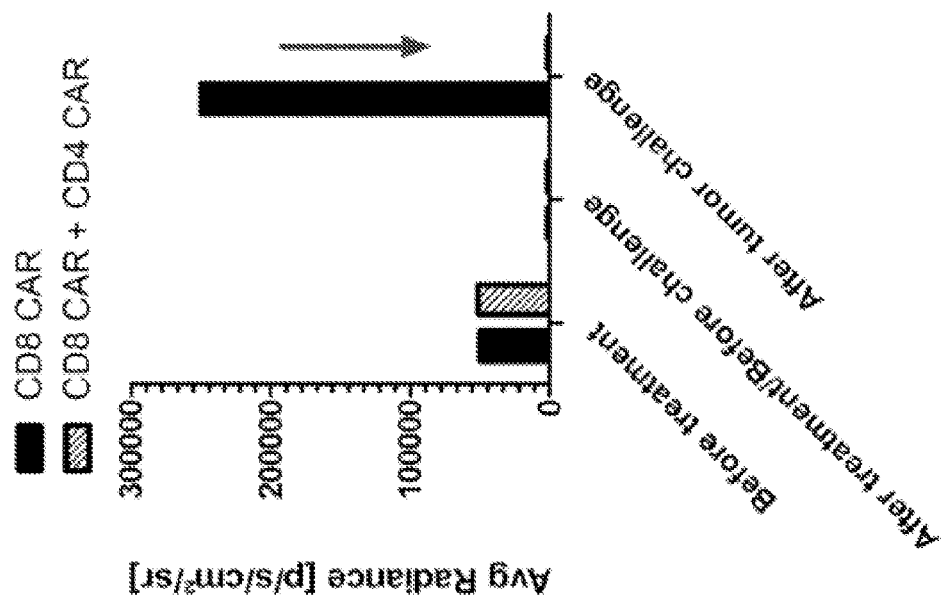
Figure 13C:
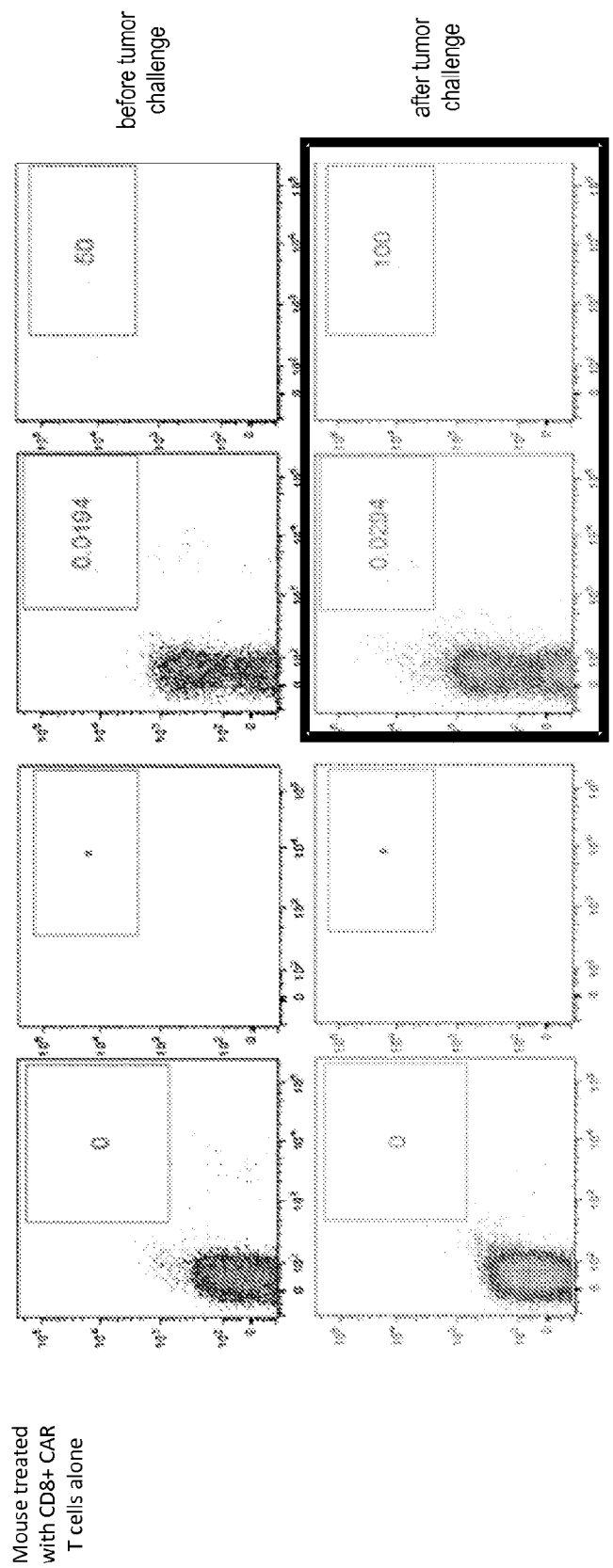
Figure 13D:
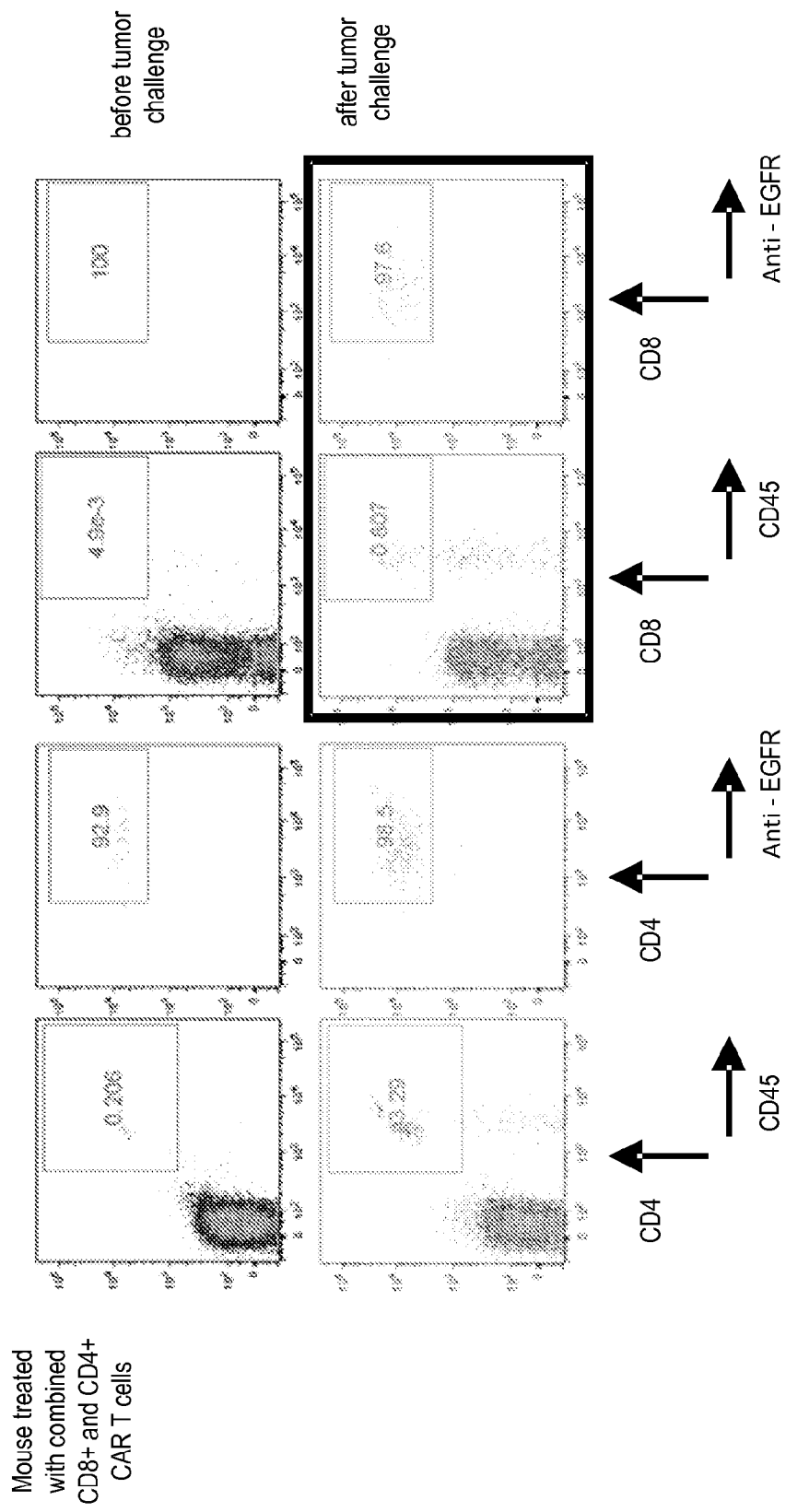

FIG. 12 shows the augmentation and synergistic effect CD4+ ROR1-CAR modified T cells on the anti-tumor efficacy of CD8+ ROR1-CAR CTLs in a mouse tumor model of systemic mantle cell lymphoma (NSG/Jeko-1-ffLuc). Anti-tumor efficacy of ROR1-CAR modified CD8+ and CD4+ T cells in a mouse tumor model of systemic aggressive mantle cell lymphoma (NSG/Jeko-1) was enhanced as compared to either cell population alone or when compared to untransduced cells.

FIG. 13 shows synergy of CD8+ and CD4+ CD19-CAR T cells in a mouse model of systemic lymphoma (NSG/Raji). Engraftment of the Raji tumor was confirmed by bioluminescence imaging on day 6 after tumor inoculation (before treatment) (treatment scheme shown in A, tumor engraftment by bioluminescence shown in B). Analysis of tumor burden using bioluminescence imaging showed complete eradication of the Raji tumors in the cohorts of mice treated with CD8+ CD19-CAR T cells, and in mice treated with the combined CD8+ and CD4+ CD19-CAR T-cell product (after treatment middle black and grey bars) B). The mice were then challenged with a second inoculum of Raji tumor cells and the frequency of CD4+ and CD8+ CAR T cells in the peripheral blood, and tumor engraftment were analyzed. In mice treated with a combined CD8+ and CD4+ CAR T-cell product, significantly higher levels CD8+ CAR T cells after the tumor challenge (C lower panels), and complete rejection of the Raji inoculum (after tumor challenge right grey bar, B). In contrast, in mice that had received CD8+ CD19-CAR CTL alone, we did not detect an increase in CAR T cells after the tumor challenge (C) and the Raji tumor cells were able to engraft (after tumor challenge right black bar, panel B).

Discussion

Collectively, these data demonstrate that transducing the cells with another CAR construct, CD19, CD19-CAR modified CD4+ and CD8+ T cells confer potent anti-tumor responses in an in vivo model of aggressive systemic lymphoma and provide evidence for a beneficial and synergistic effect of CD4+ CAR T cells on the anti-tumor efficacy of CD8+ CAR CTL.

The foregoing is illustrative of the present invention, and is not to be construed as limiting thereof. The invention is defined by the following claims, with equivalents of the claims to be included therein. All references and documents referred to herein are hereby incorporated by reference.

REFERENCES

1. Cheever, M. A., et al., Specificity of adoptive chemoimmunotherapy of established syngeneic tumors. *J. Immunol.* 125, 711-714 (1980).
2. Pahl-Seibert, M.-F. et al. Highly protective in vivo function of cytomegalovirus IE1 epitope-specific memory CD8 T cells purified by T-cell receptor-based cell sorting. *J. Virol.* 79, 5400-5413 (2005).
3. Riddell, S R. et al. Restoration of viral immunity in immunodeficient humans by the adoptive transfer of T cell clones. *Science* 257, 238-241 (1992).
4. Walter, E. A. et al. Reconstitution of cellular immunity against cytomegalovirus in recipients of allogeneic bone marrow by transfer of T-cell clones from the donor. *N Engl. J. Med.* 333, 1038-1044 (1995).
5. Rooney, C. M. et al. Infusion of cytotoxic T cells for the prevention and treatment of Epstein-Barr virus-induced lymphoma in allogeneic transplant recipients. *Blood* 92, 1549-1555 (1998).
6. Dudley, M. E. et al. Cancer regression and autoimmunity in patients after clonal repopulation with antitumor lymphocytes. *Science* 298, 850-854 (2002)/7.
7. Bollard, C. M. et al. Cytotoxic T lymphocyte therapy for Epstein-Barr virus+Hodgkin's disease. *J. Exp. Med.* 200, 1623-1633 (2004).
8. Dudley, M. E. et al. Adoptive cell transfer therapy following nonmyeloablative but lymphodepleting chemotherapy for the treatment of patients with refractory metastatic melanoma. *J. Clin. Oncol.* 23, 2346-2357 (2005).
9. Gattinoni, L., Powell Jr, D. J., Rosenberg, S. A., & Restifo, N. P. Adoptive immunotherapy for cancer: building on success. *Nat. Rev. Immunol.* 6, 383-393 (2006).
10. Blattman, J. N. & Greenberg, P. D. Cancer Immunotherapy: A treatment for the masses. *Science* 305, 200-205 (2004).
11. Kessels, H. W. H. G. et al. Immunotherapy through TCR gene transfer. *Nat. Immunol.* 2, 957-961 (2001).
12. Stanislawski, T. et al. Circumventing tolerance to a human MDM2-derived tumor antigen by TCR gene transfer. *Nat. Immunol,* 2, 962-970 (2001).
13. Brentjens, R. J. et al. Eradication of systemic B-cell tumors by genetically targeted human T lymphocytes co-stimulated by CD80 and interleukin-15. *Nat. Med.* 9, 279-286 (2003).
14. Morgan, R. A. et al. Cancer regression in patients after transfer of genetically engineered lymphocytes. *Science* advance online publication August 31, (2006). DOI: 10.1126/science. 1129003
15. Bleakley, M. & Riddell, S. R. Molecules and mechanisms of the graft versus leukemia effect. *Nat. Rev. Cancer* 4, 371-380 (2004).
16. Dudley, M. E. et al. Adoptive transfer of cloned melanoma-reactive T lymphocytes for the treatment of patients with metastatic melanoma. *J. Immunother.* 24, 363-373 (2001).
17. Yee, C. et al. Adoptive T cell therapy using antigen-specific CD8+ T cell clones for the treatment of patients with metastatic melanoma: In vivo persistence, migration, and antitumor effect of transferred cells. *Proc. Natl. Acad. Sci. USA* 99, 16168-16173 (2002).
18. Sallusto, F. et al., Central memory and effector memory T cell subsets: function, generation, and maintenance. *Annu. Rev. Immunol.* 22, 745-763 (2004).
19. Butcher, E. C. & Picker, L. J. Lymphocyte homing and homeostasis. *Science* 272, 60-66 (1996).
21. Dudley, M. E. et al. A phase I study of nonmyeloablative chemotherapy and adoptive transfer of autologous tumor antigen-specific T lymphocytes in patients with metastatic melanoma. *J. Immunother.* 25, 243-251 (2002).

22. Gattinorti, L. et al. Acquisition of full effector function in vitro paradoxically impairs the in vivo antitumor efficacy of adoptively transferred CD8+ T cells. *J. Clin. Invest.* 115, 1616-1626 (2005).
23. Schmitt T M, Ciofani M, Petrie H T, Zuniga-Plucker J C. Maintenance of T cell specification and differentiation requires recurrent notch receptor-ligand interactions. *J Exp Med.* 2004; 200(4):469-479.
24. Wang J, Press O W, Lindgren C G, et al. Cellular immunotherapy for follicular lymphoma using genetically modified CD20-specific CD8+ cytotoxic T lymphocytes. *Mol Ther.* 2004; 9(4): 577-586.
25. Riddell S R, Greenberg P D. The use of anti-CD3 and anti-CD28 monoclonal antibodies to clone and expand human antigen-specific T cells. *J Immunol Methods.* 1990; 128(2):189-201.
26. Baskar S, Kwong K Y, Hofer T, et al. Unique cell surface expression of receptor tyrosine kinase ROR1 in human B-cell chronic lymphocytic leukemia. *Clin Cancer Res.* 2008; 14(2):396-404.
27. Klein U, Tu Y, Stolovitzky G A, et al. Gene expression profiling of B cell chronic lymphocytic leukemia reveals a homogeneous phenotype related to memory B cells. *J Exp Med.* 2001; 194(11):1625-1638.
28. Rosenwald A, Alizadeh A A, Widhopf G, et al. Relation of gene expression phenotype to immunoglobulin mutation genotype in B cell chronic lymphocytic leukemia. *J Exp Med.* 2001;
29. Fukuda T, Chen L, Endo T, et al. Antisera induced by infusions of autologous Ad-CD154-leukemia B cells identify ROR1 as an oncofetal antigen and receptor for Wnt5a. *Proc Natl Acad Sci USA.* 2008; 105(8):3047-3052.
30. Lapalombella R, Andritsos L, Liu Q, et al. Lenalidomide treatment promotes CD154 expression on CLL cells and enhances production of antibodies by normal B cells through a PI3-kinase-dependent pathway. *Blood.* 2010; 115(13):2619-2629.
31. Berger C, Jensen M C, Lansdorp P M, Gough M, Elliott C, Riddell SR. Adoptive transfer of effector CD8+ T cells derived from central memory cells establishes persistent T cell memory in primates. *J Clin Invest.* 2008; 118(1):294-305.

That which is claimed is:

1. An adoptive cellular immunotherapy composition containing chimeric antigen receptor-modified CD4$^+$ T lymphocytes and chimeric antigen receptor-modified CD8$^+$ T lymphocytes, wherein:
   (a) the chimeric antigen receptor-modified CD4+ T lymphocytes contain a chimeric antigen receptor that specifically binds to an antigen and at least 50% of the chimeric antigen receptor-modified CD4+ helper T lymphocytes in the composition are surface positive for CD62L and/or CD45RA, and
   (b) the chimeric antigen receptor-modified CD8+ T lymphocytes contain a chimeric antigen receptor that specifically binds to the antigen and at least 50% of CD8+ cytotoxic T lymphocytes in the composition are surface positive for CD62L and/or CD45RO.

2. The adoptive cellular immunotherapy composition according to claim 1, wherein the antigen is associated with a disease or disorder selected from a solid tumor, hematologic malignancy, melanoma, and infection with a pathogen.

3. The adoptive cellular immunotherapy composition according to claim 1, wherein the antigen is selected from ROR1, tEGFR, Her2, L1-CAM, CD19, CD20, CD22, mesothelin, and CEA.

4. The adoptive cellular immunotherapy composition according to claim 1, wherein the chimeric antigen receptor of (a) and/or (b) comprises an extracellular antibody variable domain or single-chain antibody fragment specific for the antigen and an intracellular signaling module.

5. The adoptive cellular immunotherapy composition according to claim 4, wherein each of the intracellular signaling module of the chimeric antigen receptor contained by the CD4+ T lymphocytes and the intracellular signaling module of the chimeric antigen receptor contained by the CD8+ T lymphocytes, individually, comprise (a) a CD28 costimulatory domain and a CD3 intracellular signaling domain, or (b) a 4-1BB costimulatory domain and a CD3 intracellular signaling domain.

6. The adoptive cellular immunotherapy composition according to claim 1, wherein:
   (a) at least 60% of the chimeric antigen receptor-modified CD4$^+$ T lymphocytes are surface positive for CD62L and/or CD45RA;
   (b) at least 60% of the chimeric antigen receptor-modified CD8$^+$ cytotoxic T lymphocytes are surface positive for CD62L and/or CD45RO;
   (c) at least 80% of the chimeric antigen receptor-modified CD4+ T lymphocytes are surface positive for CD62L and/or CD45RA; and/or
   (d) at least 80% of the chimeric antigen receptor-modified CD8$^+$ cytotoxic T lymphocytes are surface positive for CD62L and/or CD45RO.

7. The adoptive cellular immunotherapy composition according to claim 1, wherein the intracellular signaling domain of the chimeric antigen receptor contained by the CD8+ T lymphocytes is the same as the intracellular signaling domain of the chimeric antigen receptor contained by the CD4+ T lymphocytes.

8. The adoptive cellular immunotherapy composition according to claim 1, wherein the CD4+ helper T lymphocytes and the CD8+ cytotoxic T lymphocytes are derived from a subject and wherein the CD4$^+$ helper T lymphocytes secrete a greater amount of IL-2 and/or exhibit a greater degree of proliferation when cultured in the presence of the antigen as compared to a reference population of CD4$^+$ T cells that has been expanded in vitro from an effector memory T cell-enriched CD4$^+$ T cell population or a bulk CD4$^+$ T cell population from the subject and modified to contain the chimeric antigen receptor contained by the CD4+ helper T lymphocytes.

9. The adoptive cellular immunotherapy composition of claim 1, wherein at least 50% of the chimeric antigen receptor-modified CD4+ helper T lymphocytes in the composition are surface positive for CD62L.

10. The adoptive cellular immunotherapy composition of claim 1, wherein at least 50% of the chimeric antigen receptor-modified CD8+ cytotoxic T lymphocytes in the composition are surface positive for CD62L.

11. The adoptive cellular immunotherapy composition of claim 1, wherein at least 50% of the chimeric antigen receptor-modified CD4+ helper T lymphocytes in the composition are surface positive for CD62L and at least 50% of the chimeric antigen receptor-modified CD8+ cytotoxic T lymphocytes in the composition are surface positive for CD62L.

12. The adoptive cellular immunotherapy composition of claim 1, wherein at least 60% of the chimeric antigen receptor-modified CD4+ helper T lymphocytes in the composition are surface positive for CD62L and/or at least 60% of the chimeric antigen receptor-modified CD8+ cytotoxic T lymphocytes in the composition are surface positive for CD62L.

13. The adoptive cellular immunotherapy composition of claim 1, wherein at least 80% of the chimeric antigen receptor-modified CD4+ helper T lymphocytes in the composition are surface positive for CD62L and/or at least 80% of the chimeric antigen receptor-modified CD8+ cytotoxic T lymphocytes in the composition are surface positive for CD62L.

14. The adoptive cellular immunotherapy composition of claim 1, wherein the chimeric antigen receptor-modified CD4+ helper T lymphocytes in the composition and the chimeric antigen receptor-modified CD8+ cytotoxic T lymphocytes are present in the composition at a ratio of between about 2:1 to about 1:2.

15. The adoptive cellular immunotherapy composition of claim 1, wherein the chimeric antigen receptor-modified CD4+ helper T lymphocytes in the composition and the chimeric antigen receptor-modified CD8+ cytotoxic T lymphocytes are present in the composition at a ratio of about 2:1, 1:1, or 1:2.

16. The adoptive cellular immunotherapy composition of claim 1, wherein the chimeric antigen receptor contained by the CD8+ T lymphocytes is the same as the chimeric antigen receptor contained by the CD4+ T lymphocytes.

17. The adoptive cellular immunotherapy composition of claim 1, wherein the intracellular signaling domain of the chimeric antigen receptor in the CD8+ T lymphocytes is different from the intracellular signaling domain of the chimeric antigen receptor in the CD4+ T lymphocytes; or the chimeric antigen receptor contained by the CD8+ T lymphocytes is different than the chimeric antigen receptor contained by the CD4+ T lymphocytes.

18. The adoptive cellular immunotherapy composition according to claim 1, wherein the antigen is ROR1.

19. The adoptive cellular immunotherapy composition according to claim 1, wherein the antigen is Her2.

20. The adoptive cellular immunotherapy composition according to claim 1, wherein the antigen is L1-CAM.

21. The adoptive cellular immunotherapy composition according to claim 1, wherein the antigen is CD19.

22. The adoptive cellular immunotherapy composition according to claim 1, wherein the antigen is CD20.

23. The adoptive cellular immunotherapy composition according to claim 1, wherein the antigen is CD22.

24. The adoptive cellular immunotherapy composition according to claim 1, wherein the antigen is mesothelin.

25. The adoptive cellular immunotherapy composition according to claim 1, wherein the antigen is CEA.

26. The adoptive cellular immunotherapy composition according to claim 2, wherein the disease or disorder is a solid tumor, hematologic malignancy, or melanoma.

27. The adoptive cellular immunotherapy composition according to claim 2, wherein the disease or disorder is a hematologic malignancy.

28. The adoptive cellular immunotherapy composition according to claim 1, wherein the antigen is a tumor associated antigen associated with a cancer selected from the group consisting of melanoma, breast cancer, squamous cell carcinoma, colon cancer, leukemia, myeloma, prostate cancer, B cell lymphoma, breast cancer, prostate cancer, and leukemia.

29. The adoptive cellular immunotherapy composition according to claim 1, wherein a greater percentage of the chimeric antigen receptor-modified $CD4^+$ helper T lymphocytes are surface positive for CD62L and/or CD45RA as compared to a reference population of $CD4^+$ T cells that has been expanded in vitro from an effector memory-enriched $CD4^+$ T cell population or a bulk $CD4^+$ T cell population from the subject and modified to contain the chimeric antigen receptor contained by the CD4+ helper T lymphocytes.

30. The adoptive cellular immunotherapy composition according to claim 1, wherein a greater percentage of the chimeric antigen receptor-modified $CD8^+$ cytotoxic T lymphocytes are surface positive for CD62L, CD45RO and/or CCR7 as compared to a reference population of $CD8^+$ T cells that has been expanded in vitro from an effector memory-enriched $CD8^+$ T cell population or bulk $CD8^+$ T cell population from the subject and modified to contain the chimeric antigen receptor contained by the CD8+ cytotoxic T lymphocytes.

31. The adoptive cellular immunotherapy composition according to claim 1, wherein the chimeric antigen receptor-modified $CD8^+$ cytotoxic T lymphocytes proliferate when co-cultured in vitro with the $CD4^+$ helper T lymphocytes in the presence of the antigen, to a greater degree as compared to the degree of proliferation of the $CD8^+$ cytotoxic T lymphocytes when co-cultured, under the same conditions, with a reference population of $CD4^+$ T cells expanded in vitro from an effector memory-enriched $CD4^+$ T cell population or a bulk $CD4^+$ T cell population from the subject and modified to contain the chimeric antigen receptor contained by the CD4+ helper T lymphocytes.

* * * * *